(12) United States Patent
Kang et al.

(10) Patent No.: US 9,528,947 B2
(45) Date of Patent: Dec. 27, 2016

(54) CALIBRATION METHOD OF RADIATION DETECTING APPARATUS, RADIATION IMAGING APPARATUS AND CONTROL METHOD OF RADIATION IMAGING APPARATUS

(71) Applicant: SAMSUNG ELECTRONICS CO., LTD., Suwon-si (KR)

(72) Inventors: Sung Hoon Kang, Suwon-si (KR); Dong Goo Kang, Hwaseong-si (KR); Young Hun Sung, Hwaseong-si (KR); Sang Wook Han, Busan (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 619 days.

(21) Appl. No.: 13/893,456

(22) Filed: May 14, 2013

(65) Prior Publication Data
US 2013/0301798 A1 Nov. 14, 2013

Related U.S. Application Data

(60) Provisional application No. 61/646,476, filed on May 14, 2012.

(30) Foreign Application Priority Data

Mar. 22, 2013 (KR) ........................ 10-2013-0031071

(51) Int. Cl.
*G01N 23/04* (2006.01)
*G01T 7/00* (2006.01)

(52) U.S. Cl.
CPC .............. *G01N 23/04* (2013.01); *G01T 7/005* (2013.01)

(58) Field of Classification Search
CPC ....... A61B 6/032; A61B 6/482; A61B 6/4241; A61B 6/585; G01N 23/04; G01T 7/005
See application file for complete search history.

(56) References Cited

U.S. PATENT DOCUMENTS

| | | | |
|---|---|---|---|
| 7,632,016 B1* | 12/2009 | Huang et al. ................. | 378/207 |
| 2009/0200478 A1* | 8/2009 | Bethke .................... | G01T 1/247 250/370.09 |
| 2011/0085719 A1* | 4/2011 | Fan et al. ...................... | 382/131 |
| 2014/0185766 A1* | 7/2014 | Kang ..................... | G01T 7/005 378/62 |
| 2014/0185781 A1* | 7/2014 | Reitz ...................... | G01T 7/005 378/207 |

* cited by examiner

*Primary Examiner* — Glen Kao
(74) *Attorney, Agent, or Firm* — Sughrue Mion, PLLC

(57) ABSTRACT

A calibration method of a radiation detecting apparatus, a control method of a radiation imaging apparatus and a radiation imaging apparatus are provided. The control method of the radiation imaging apparatus includes performing prior information acquisition by obtaining at least one correction threshold energy, at which a theoretical radiation intensity of at least one threshold energy is measured, and performing radiation image acquisition by obtaining at least one radiation image at the at least one threshold energy using the at least one correction threshold energy.

21 Claims, 17 Drawing Sheets

(a) PRIOR INFORMATION ACQUISITION   (b) IMAGING

CALIBRATION METHOD OF RADIATION DETECTING APPARATUS, RADIATION IMAGING APPARATUS AND CONTROL METHOD OF RADIATION IMAGING APPARATUS

CROSS-REFERENCE TO RELATED APPLICATIONS

This application claims priority from U.S. Provisional Application No. 61/646,476, filed on May 14, 2012 and Korean Patent Application No. 2013-0031071, filed on Mar. 22, 2013 in the Korean Intellectual Property Office, the disclosures of which are incorporated herein by reference in their entirety.

BACKGROUND

1. Field

Apparatuses and methods consistent with the exemplary embodiments relate to a calibration method of a radiation detecting apparatus, a radiation imaging apparatus and a control method of a radiation imaging apparatus.

2. Description of the Related Art

When x-rays, also referred to as roentgen rays, are radiated onto an object, such as a human body, the x-rays are entirely or partially absorbed by a material which is inside of the object placed on a path of the x-rays. The amount of absorption depends on the characteristics of the material, for example, the density or the mass when the x-rays penetrate the material. A radiography apparatus represents an imaging apparatus, which by use of the x-ray properties, receives the penetrated radiation and obtains an image of the inside of the object based on the data about the received penetrated radiation. The radiography apparatus can be used to detect or diagnose an abnormality, such as a lesion, on the inside of the human body, or to scan the inside of luggage in an airport.

As for the operation principle of the radiography apparatus, after x-rays are radiated onto an object, such as a human body, the radiography apparatus receives x-rays which have passed through the object or x-rays directed around the object, converts the received x-rays into electric signals, generates an x-ray image by reading out the converted electric signal, and then displays the generated x-ray image to a user to provide the x-ray image. Examples of the radiography apparatus include a digital radiography (DR) apparatus, a computed tomography (CT) apparatus, and a full field digital mammography (FFDM) apparatus.

SUMMARY

Therefore, exemplary embodiments provide a radiation imaging apparatus, a control method of a radiation imaging apparatus and a calibration method of a radiation detecting apparatus used to detect radiation, capable of obtaining a desired image of the inside an object.

Other exemplary embodiments provide a radiation imaging apparatus, a control method of a radiation imaging apparatus and a calibration method of a radiation detecting apparatus used to detect radiation, capable of finely adjusting threshold energy in detecting radiation.

Additional aspects of the disclosure will be set forth in part in the description which follows and, in part, will be obvious from the description, or may be learned by practice of the disclosure.

In accordance with an aspect of an exemplary embodiment, a method of controlling a radiation imaging apparatus is as follows. Prior information acquisition may be performed by obtaining at least one correction threshold energy, at which a theoretical radiation intensity of at least one threshold energy is measured. Radiation image acquisition may be performed by obtaining at least one radiation image at the at least one threshold energy using the at least one correction threshold energy.

When performing the prior information acquisition, a radiation intensity of the at least one correction threshold energy may be obtained. When performing the radiation image acquisition, at least one radiation image at the at least one threshold energy may be generated using the radiation intensity of the at least one correction threshold energy.

When performing the prior information acquisition, radiation intensities of a plurality of threshold energies with respect to at least one material composition may be obtained. The plurality of threshold energies may include the at least one threshold energy.

When performing the radiation image acquisition, a material composition of the object may be determined using the at least one of the plurality of threshold energies with the obtained radiation intensities.

When performing the radiation image acquisition, at least one calibrated radiation image may be generated at the at least one threshold energy using the determined material composition of the object and the at least one correction threshold energy.

When performing the radiation image acquisition, an image calibration value may be generated based on a radiation intensity of the at least one correction threshold energy, and at least one calibration radiation image may be generated at the at least one threshold energy using the determined material composition of the object and the at least one correction threshold energy.

When performing of radiation image acquisition, the image calibration value may be generated based on a relationship between a radiation intensity of the correction threshold energy and a radiation intensity of the at least one threshold energy.

In accordance with another aspect of an exemplary embodiment, a method of controlling a radiation imaging apparatus is as follows. Radiography may be performed by emitting radiation onto an object, receiving the radiation and converting the received radiation into an electric signal. Radiation image generation may be performed by generating at least one radiation image at the at least one threshold energy based on the electric signal, which is converted from the radiation, and the at least one threshold energy. At least one calibrated radiation image may be generated by using the at least one correction threshold energy for the at least one threshold energy. The at least one correction threshold energy may be a threshold energy at which a theoretical radiation intensity of the at least one threshold energy is measured.

The method may further include performing a radiation intensity measurement by measuring a radiation intensity of the at least one threshold energy based on the electric signal converted from the radiation.

When performing radiation image generation, the at least one radiation image may be calibrated using the radiation intensity of the at least one threshold energy and a radiation intensity of the at least one correction threshold energy for the at least one threshold energy.

The method may further include performing a radiation intensity measurement by measuring radiation intensities of a plurality of threshold energies based on the electric signal converted from the radiation, and performing a material composition determination by determining a material composition of the object using the measured radiation intensities of the plurality of threshold energies.

When performing the radiation image generation, the radiation image of the at least one threshold energy may be generated using a radiation intensity of the at least one correction threshold energy and the determined material composition of the object.

When performing the radiation image generation, the radiation intensity of the correction threshold energy may be determined according to the radiation intensity of the at least one threshold energy and the determined material composition of the object, and the at least one radiation image may be calibrated based on the determined radiation intensity of the correction threshold energy.

When performing the radiation image generation, an image calibration value may be generated based on the radiation intensity of the at least one threshold energy, the radiation intensity of the correction threshold energy, and the determined material composition of the object, and the radiation image of the at least one threshold energy may be calibrated using the generated image calibration value.

In accordance with another aspect of an exemplary embodiment, a radiation imaging apparatus includes a radiation emitter, a radiation detector, and an image processor. The radiation emitter may be configured to emit radiation onto an object. The radiation detector may be configured to receive the radiation emitted from the radiation emitter and convert the received radiation into an electric signal according to at least one threshold energy. The image processor may be configured to generate a radiation image based on the electric signal, and calibrate the generated radiation image using at least one correction threshold energy for the at least one threshold energy. The at least one correction threshold energy may be a threshold energy at which a theoretical radiation intensity of the at least one threshold energy is measured.

The radiation emitter may emit radiation onto the object a plurality of times, and determine a material composition of the object based on a plurality of threshold energies.

The image processor may calibrate a radiation image at the at least one threshold energy using the determined material composition and the at least one correction threshold energy.

The image processor may obtain the at least one correction threshold energy using the determined material composition of the object and the at least one threshold energy.

The image processor may obtain a radiation intensity of the correction threshold energy using the determined material composition of the object and a radiation intensity of the at least one threshold energy.

The image processor may generate an image calibration value based on a radiation intensity of the at least one threshold energy and a radiation intensity of the correction threshold energy, and may calibrate the at least one radiation image using the image calibration value.

BRIEF DESCRIPTION OF THE DRAWINGS

These and/or other aspects of the disclosure will become apparent and more readily appreciated from the following description of the exemplary embodiments, taken in conjunction with the accompanying drawings of which.

DETAILED DESCRIPTION

Figure 1:
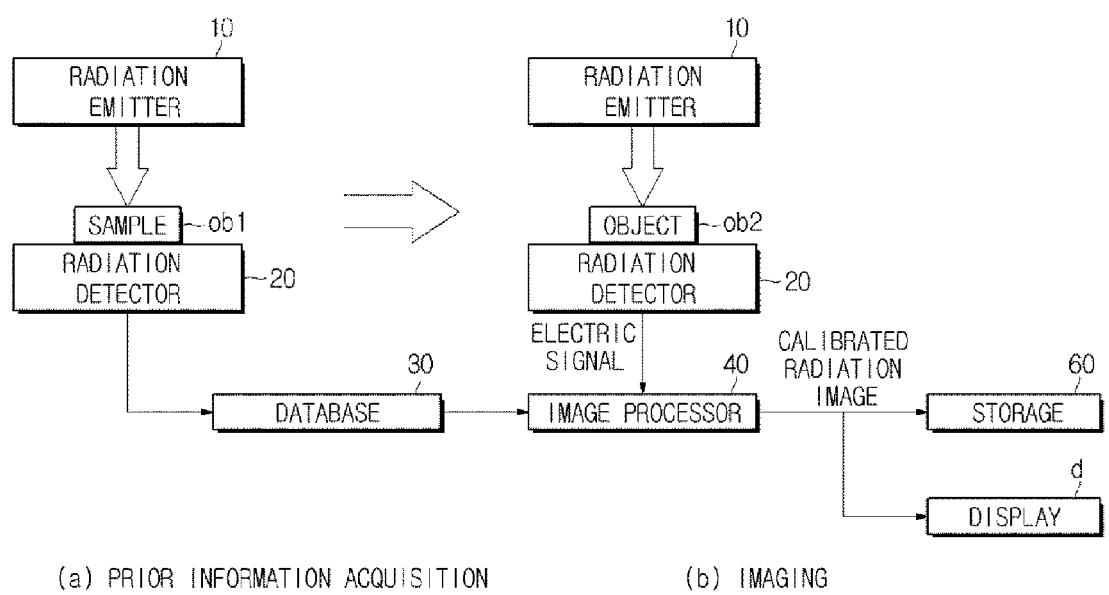
FIG. 1 is a drawing used to explain a calibration method and a control method of a radiation imaging apparatus.

Reference will now be made in detail to the exemplary embodiments, examples of which are illustrated in the accompanying drawings, wherein like reference numerals refer to like elements throughout.

Hereinafter, a control method of a radiation imaging apparatus in accordance with the exemplary embodiments will be described with reference to FIGS. 1 to 12.

FIG. 1 is a drawing used to explain prior information acquisition of a radiation imaging apparatus and a control method of a radiation imaging apparatus.

Referring to FIG. 1, the radiation imaging apparatus includes a radiation emitter 10 to emit radiation and a radiation detector 20 to detect the emitted radiation.

The radiation emitter 10 emits radiation toward the radiation detector 20 according to a setting made by a user or a predetermined setting. According to an exemplary embodiment, the radiation emitted from the radiation emitter 10 may be x-rays.

The radiation emitted from the radiation emitter 10 is entirely or partially absorbed into an object, for example, a sample ob1 or a subject ob2. The remaining radiation which is not absorbed by the object passes through the object and reaches the radiation detector 20.

The radiation detector 20 receives radiation which has passed through the sample ob1 or the subject ob2, and converts the received radiation into electric signals so that a radiation image is generated based on the converted electric signal.

The radiation detector 20 in accordance with an exemplary embodiment may represent a photon counting x-ray radiation detector.

The photon counting x-ray radiation detector is an x-ray radiation detector configured to divide x-rays, which are incident onto the photo counting x-ray radiation detector, according to photon energy bands. In detail, the photon counting x-ray radiation detector separates x-rays having a photon energy exceeding a predetermined energy, that is, exceeding a threshold energy, so that the electric signals based on the x-rays are divided according to the threshold energy.

Figure 2:
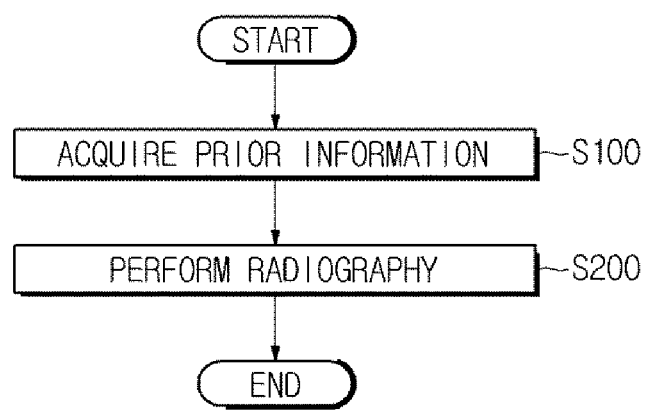
FIG. 2 is a flowchart showing a control method of a radiation imaging apparatus in accordance with an exemplary embodiment.

FIG. 2 is a flowchart showing a control method of a radiation imaging apparatus in accordance with an exemplary embodiment.

Referring to FIGS. 1 and 2, a control method of a radiation imaging apparatus in accordance with an exemplary embodiment includes performing a prior information acquisition (see FIG. 1 (*a*) and operation S100 in FIG. 2), and performing a radiation image capturing (see FIG. 1(*b*) and operation S200 in FIG. 2). Operation S100 of acquiring prior information and operation S200 of capturing a radiation image may be each performed by the same radiation imaging apparatus, or depending on the situation, may be performed by a different radiation imaging apparatus.

First, in operation S100 of acquiring prior information as shown in FIG. 2, radiation is emitted to acquire prior information that is used to calibrate a radiation image. An object on which the radiation is emitted in operation S100 may be the sample ob1.

Figure 3:
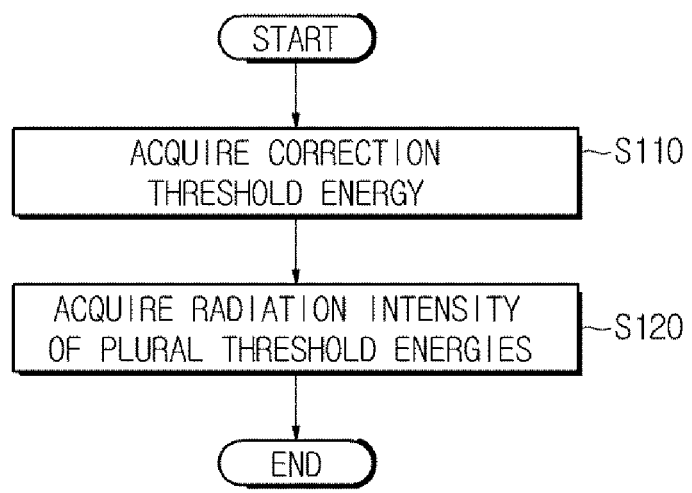
FIG. 3 is a flowchart showing a prior information acquisition operation in accordance with an exemplary embodiment.

FIG. 3 is a flowchart showing a prior information acquisition operation in accordance with an exemplary embodiment.

Referring to FIG. 3, operation S100 of acquiring prior information as discussed in FIG. 2, includes acquiring a correction threshold energy (S110). In accordance with an exemplary embodiment, operation S100 of acquiring prior information may further include acquiring radiation intensities of a plurality of threshold energies (S 120).

In operation S110 of acquiring a correction threshold energy, an actual measurement threshold energy, at which the same radiation intensity as a theoretical radiation intensity of a predetermined threshold energy is measured, is measured, and the measured actual measurement threshold energy is determined as the correction threshold energy.

Hereinafter, the radiation detector 20 in accordance with an exemplary embodiment will be described in more detail to explain operation S110 of acquiring the correction threshold energy.

Figure 4:
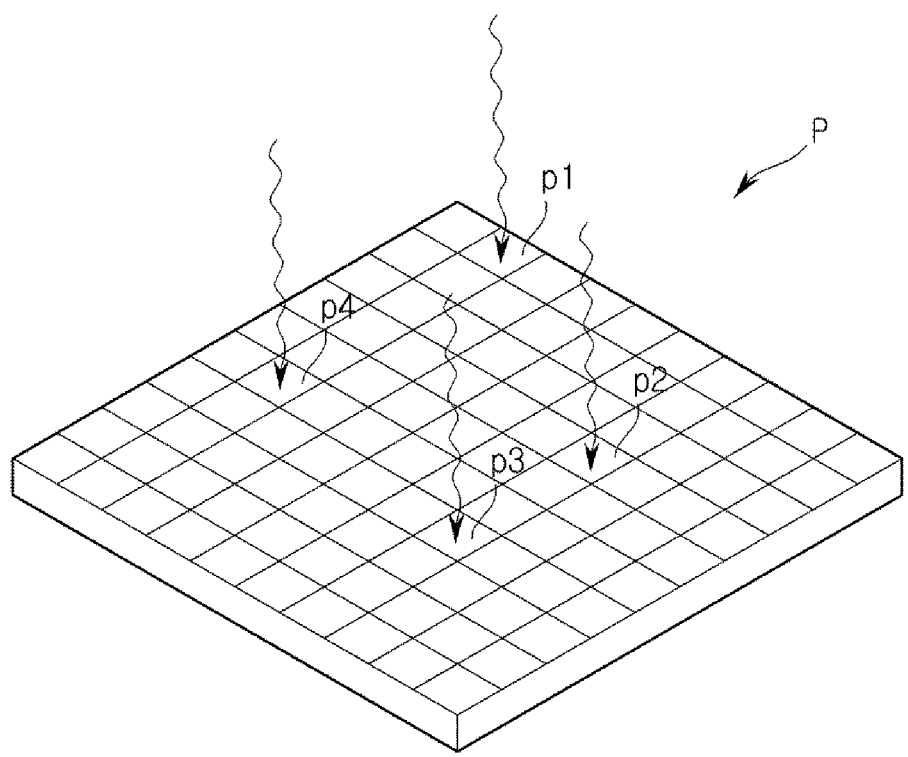
FIG. 4 is a drawing illustrating a radiation detecting panel of a radiation detecting apparatus in accordance with an exemplary embodiment.
Figure 5:
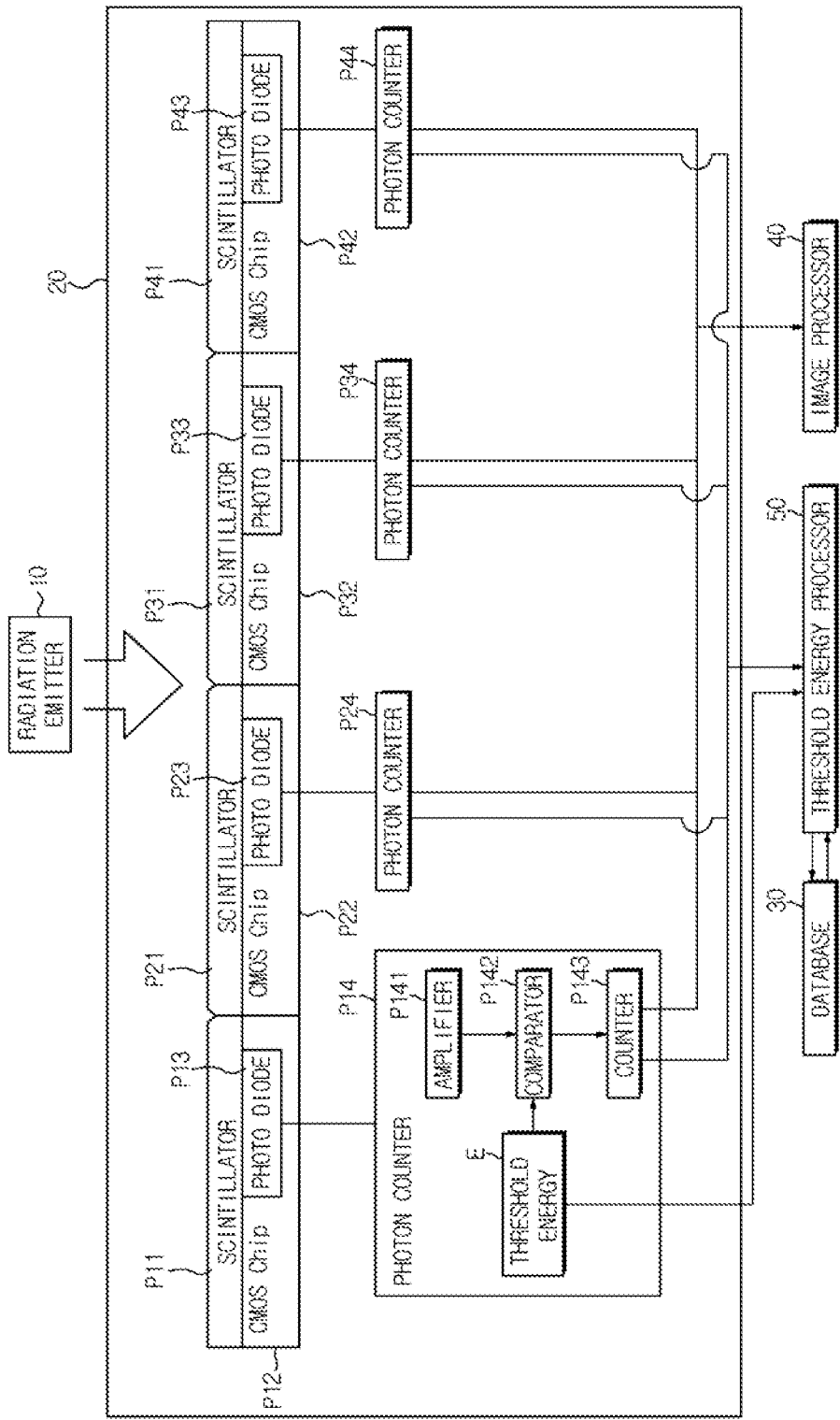
FIG. 5 is a block diagram illustrating a radiation detecting apparatus in accordance with an exemplary embodiment.

FIG. 4 is a drawing illustrating a radiation detecting panel of a radiation detector in accordance with an exemplary embodiment. FIG. 5 is a block diagram illustrating a radiation detector in accordance with an exemplary embodiment.

The radiation detector 20, as shown in FIG. 5, may be provided with a radiation detecting panel p as shown in FIG. 4 to detect the radiation emitted from the radiation emitter 10.

The radiation detecting panel p may be composed of a plurality of pixels p1 to p4 to detect the radiation reaching the radiation detecting panel p. The plurality of pixels p1 to p4 receive the emitted radiation, and each pixel outputs an electric signal corresponding to the received radiation. In this case, each of the pixels p1 to p4 may output an electric signal corresponding to a respective pixel of a radiation image that is to be generated.

In more detail, each of the pixels p1, p2, p3, and p4 may respectively include a scintillator p11, a scintillator p21 a scintillator p31 and a scintillator p41. Further, each of pixels p1, p2, p3, and p4 may respectively include a photo conductor p13, a photo conductor p23, a photo conductor p33, and a photo conductor p43. Scintillator p11, scintillator p21, scintillator p31 and scintillator p41, and photo conductor p13, photo conductor p23, photo conductor p33, and photo conductor p43, are respectively installed on a complementary metal oxide semiconductor (CMOS) chip p12, CMOS chip p22, CMOS chip p32, and CMOS chip p42 as shown in FIG. 5.

The scintillator p11 is a material that emits scintillation according to the reception of radiation. The scintillator p11 receives a radiation photon emitted from the radiation emitter 10, for example, x-ray photons, and outputs a predetermined visible ray according to the received x-ray photon.

The photo conductor p13 receives the predetermined visible ray output from the scintillator p11, and outputs a predetermined electric signal V in a unit of millivolt (mV) corresponding to the received predetermined visible ray. An image processor 40, which is to be described later, outputs a radiation image based on the electric signal which is output.

The electric signal V output from the photo conductor p13 may be determined by the photon energy E of radiation in a unit of kiloelectron volt (keV). In this case, a predetermined relation, which is referred to as keV-mV relation, is formed between the photon energy E of radiation and the electric signal V.

The photo conductor p13 in accordance with an exemplary embodiment may be a photodiode as shown in FIG. 5.

The electric signal output from the photo conductor p13 is transmitted to a photon counter p14.

The photon counter p14 measures the number of photons of radiation exceeding a threshold energy, thereby analyzing the radiation photons according to energy bands.

In detail, the photon counter p14 measures the number of photons of radiation exceeding a threshold energy, and outputs an electric signal, which is obtained from radiation exceeding the threshold energy according to the result of measurement. Therefore, the radiation photons are divided according to energy bands.

In accordance with an exemplary embodiment, the photo conductor p13 of each of the pixels p1 to p4 may be connected to the respective photon counter p14. In this case, each photon counter p14 may analyze the electric signal output from each of the pixels p1 to p4, according to the energy bands.

In accordance with an exemplary embodiment, the photon counter p14 may include an amplifier p141, a comparator p142 and a counter p143 as shown in FIG. 5.

The amplifier p141 amplifies the electric signal output from the photo conductor p13 so that an electric signal having an amplified predetermined voltage is output.

The comparator p142 may compare the electric signal amplified by the amplifier p141 with a threshold energy E to determine whether the amplified electric signal is greater or smaller than the threshold energy and to output a signal obtained as a result of the comparison. In accordance with an exemplary embodiment, threshold energies respectively compared with the electric signals output from each of the pixels p1 to p4 may have the same magnitude.

Meanwhile, in accordance with an exemplary embodiment, a voltage of the electric signal may be compared with a threshold voltage corresponding to a threshold energy to determine whether the electric signal is greater or smaller than the threshold energy. The threshold voltage may be acquired by converting the threshold energy according to the above described keV-mV relation.

The comparator p142 may generate a binary signal according to the determination result. For example, if determined from the comparison between the threshold energy and the electric signal that the electric signal is equal to or greater than the threshold energy, the comparator p142 may output a signal of 1, and if determined that the electric signal is smaller than the threshold energy, may output a signal of 0. The signal according to the determination result of comparison, that is, the binary signal output from the comparator p142 is transmitted to the counter p143.

The counter p143 counts photons exceeding the threshold energy according to the signal transmitted from the comparator p142, and outputs result information about the photons being counted. The result information about the photons being counted may be used as the radiation intensity. In accordance with an exemplary embodiment, the counter p143 may count only the signal, output from the comparator p142, each having a value of 1, thereby counting photons each of which is greater than the threshold energy.

The radiation intensity output from the photon counter p14 of the radiation detector 20 is transmitted to the image processor 40, and the image processor 40 generates an image based on the radiation intensity.

In detail, the image processor 40 generates a radiation image based on the information from the counting result, that is, based on the radiation intensity. For example, the image processor 40 generates a radiation image by applying a predetermined color to each of the pixels p1 to p4 according to the radiation intensity of each of the pixels p1 to p4. In detail, if the number of photons counted with respect to a certain pixel, for example, p1 is 0 or almost 0, that is, if the radiation intensity is low, the image processor 40 allows a relatively dark color, for example, black to be displayed on a pixel of an image corresponding to the pixel p1.I If the number of photons counted is large, that is, the radiation intensity is high, the image processor 40 allows a relatively bright color, for example, white to be displayed on a pixel of an image corresponding to the pixel p1.

The image processor 40 may be a processor installed at the radiation detector 20. Alternatively, the image processor 40 may be a processor installed at a workstation connected to the radiation detector 20 in a wired/wireless communication network.

However, even if the same radiation passes through the same object, the number of photons counted by the counter p143 may not be same as the number of photons counted in an ideal condition. The number of photons which are counted may vary with the hardware characteristics of the radiation detecting panel p or a circuit installed on the radiation detector 20 because the magnitude of the electric signal output from each of the pixels p1 to p4 of the radiation detecting panel p may be affected by the respective characteristics of the components of the radiation detecting panel p. That is, the respective characteristics of components such as the scintillator p11, the photo conductor p13 and the photon counter p14 of each pixel p1 to p4.

For example, even if radiation of the same energy is emitted, the scintillator p11 of each of the pixels p1 to p4 may output a different visible ray even to a small degree. In addition, even if the photo conductor p13 of each of the pixels p1 to p4 receives the same visible ray, the photo conductor p13 may output a different electric signal even to a small degree. Accordingly, the electric signal compared by the comparator p142 may be smaller or greater than an electric signal in an ideal condition.

That is, each of the pixels p1 to p4 of the radiation detecting panel p, even upon reception of the same energy radiation photon, may output a different electric signal according to an external influence. Accordingly, the relation between the received photon energy and the electric signal being output, that is keV-mV, may be different among the respective pixels p1 to p4.

Meanwhile, a threshold voltage V, which is converted from the threshold energy E by use of the keV-mV relation, may be used by the comparator p142 to compare the electric signal of each of the pixels p1 to p4. When the threshold energies E respectively used for comparison with the electric signals of the pixels p1 to p4 are the same, threshold voltages V respectively used for comparison with the electric signals output from each of the pixels p1 to p4 may be also the same. Accordingly, the same threshold voltage V is used for comparison with the electric signals output from the pixels p1 to p4.

As described above, if the electric signals which are output are different at the respective pixels p1 to p4, the keV-mV relations may be different at the respective pixels p1 to p4. In this case, using the same threshold voltage V as a threshold voltage to be compared in the comparator p142 produces a result as if the photon counting is performed on each pixel p1 to p4 by use of a different threshold energy, and thus producing an error in the resultant signal of counting.

In detail, for example, if an electric signal output from the photo conductor p13 is output while having a voltage smaller than a voltage of an electric signal in an ideal condition due to the hardware characteristics of the photo conductor p13 of a certain pixel p1, the comparator p142 compares the electric signal which is smaller than the electric signal in the ideal condition with a threshold voltage in an ideal condition. Therefore, the comparator p143 outputs fewer signals each having a value of 1. Accordingly, the number of photons counted by the counter p143 is lower than the number of photons counted in an ideal condition. Accordingly, the precision and reliability of the signals output from the comparator p142 is lowered, and thus the precision and reliability of the signals output from the counter p143 is lowered.

Accordingly, a radiation image generated from the image processor 40, which is to be described later, may be different from a radiation image acquired in an ideal condition, thereby causing an artifact on the radiation image.

In order to calibrate such an artifact on the radiation image, a correction threshold energy may be used.

The correction threshold energy $E_C$ represents a threshold energy at which a theoretical radiation intensity of a predetermined threshold energy $E_0$ is measured.

A radiation intensity used to generate a radiation image in the radiation imaging apparatus is expressed through equation 1 below.

$$I = I_0 e^{-\mu t} \quad \text{[Equation 1]}$$

$I_0$ represents the intensity of radiation which is input, that is, the intensity of radiation reaching the radiation detector 20 in the absence of the sample ob1 or the subject ob2.

I represents the intensity of radiation passing through the sample ob1 or the subject ob2, that is, the intensity of radiation according to attenuation with a part of the radiation absorbed while passing through the sample ob1 or the subject ob2.

Meanwhile, μ represents the attenuation rate of the sample ob1 or the subject ob2, and t represents the thickness of the sample ob1 or the subject ob2.

The normalized intensity is defined as the ratio between I and $I_0$ through equation 2 below.

$$I_{normal} = \frac{I}{I_0} \quad \text{[Equation 2]}$$

The intensity of radiation or the normalized intensity of radiation may vary with the threshold energy. The intensity of radiation or the normalized intensity of radiation with respect to the threshold energy may be expressed in the form of a graph having each of the radiation intensity or the normalized radiation intensity and the threshold energy as an axis.

Figure 6:
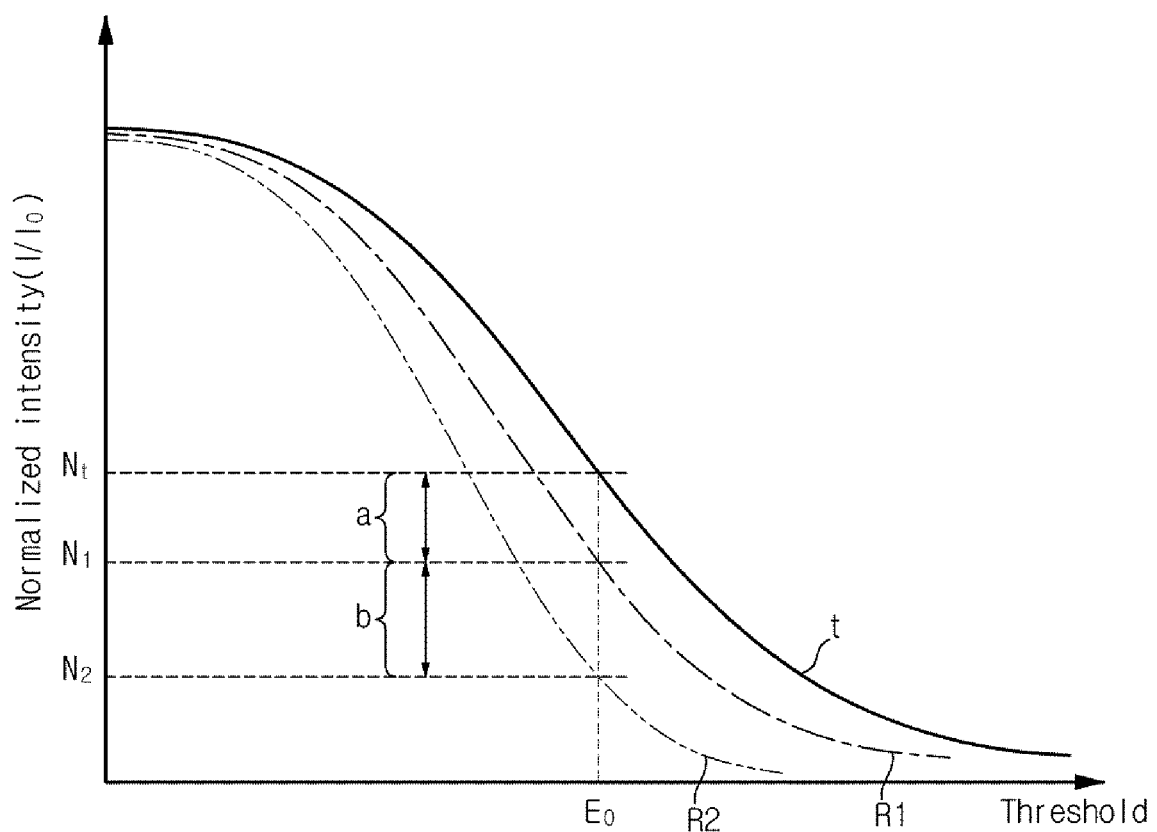
FIGS. 6 and 7 are graphs showing a relationship between the threshold energy and the radiation intensity.
Figure 7:
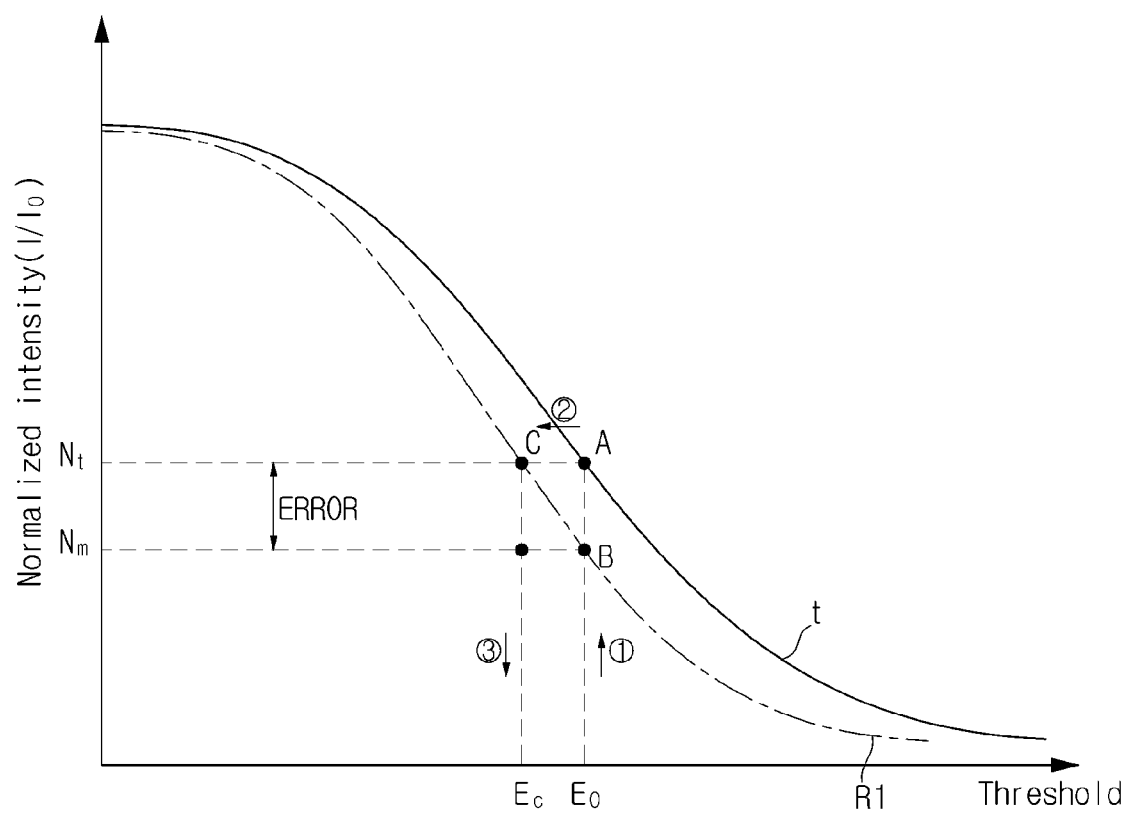

FIGS. 6 and 7 are graphs showing a relationship between the threshold energy and the normalized radiation intensity.

Referring to FIGS. 6 and 7, the x-axis represents the threshold energy, and the y-axis represents the normalized radiation intensity. Meanwhile, a curve t represents a change of the normalized radiation intensity with respect to the threshold energy keV in an ideal condition. Curves R1 and R2 respectively represent changes of the normalized radiation intensities with respect to the threshold energies measured in practice by use of a first pixel p1 and a second pixel p2, respectively.

Referring to FIG. 6, the curve t between the threshold energy in an ideal condition and the normalized radiation intensity may be different from the curve R1 between the threshold energy measured in practice and the normalized radiation intensity. In addition, the curves R1 and R2 between the threshold energy measured by respective pixels in practice and the normalized radiation intensity may be different. Such a difference is caused by the physical characteristics and hardware characteristics of each of the pixels p1 to p4 of the radiation detecting panel p or each circuit.

Accordingly, an ideal normalized intensity of radiation $N_t$ calculated depending on a predetermined threshold energy $E_0$ is different from a normalized intensity $N_1$ of radiation acquired at the first pixel p1. Therefore, a predetermined error (a) is generated as shown in FIG. 6. Similarly, a predetermined error (a)+(b) as shown in FIG. 6 exists between the ideal normalized intensity of radiation $N_t$ and a normalized intensity $N_2$ of radiation acquired at the second pixel p2.

In order to prevent such errors, a correction threshold energy $E_c$ is acquired as shown in FIG. 7.

Referring to FIG. 7, an ideal normalized intensity of radiation for the predetermined threshold energy $E_0$ is given as $N_t$ (see point A). However, the normalized intensity of radiation measured through the first pixel p1 in practice is given as Nm (see point B) while varying along the curve R1 between the photon energy for the first pixel and the normalized intensity of radiation.

In this case, the correction threshold energy is given as $E_c$ on the x-axis (see point C), at which a normalized intensity of radiation identical to the normalized intensity $N_t$ of radiation of the predetermined threshold energy $E_0$ is acquired, while moving on the curve R1 between the photon energy for the first pixel p1 and the normalized intensity of radiation.

Accordingly, by using the correction threshold energy $E_c$ for the predetermined threshold energy $E_0$, the errors generated due to the hardware characteristics of each component of the radiation detector 20, that is, each of the pixels p1 to p4, are calibrated.

For example, if the comparator p142 compares the electric signal with the correction threshold energy $E_c$ instead of with the predetermined threshold energy $E_0$, a radiation image identical or similar to a radiation image taken in an ideal condition is acquired.

Referring to FIG. 5, a threshold energy processor 50 determines a correction threshold energy $E_c$ for a predetermined threshold energy $E_o$, and stores the determined correction threshold energy $E_c$ in the database 30.

The database 30 in which the determined correction threshold energy $E_c$ is stored may be constructed while being stored in various memory units installed on the radiation imaging apparatus or the radiation detector 20, or constructed while being stored in an external information processing device, such as a workstation or a server device.

Figure 8:
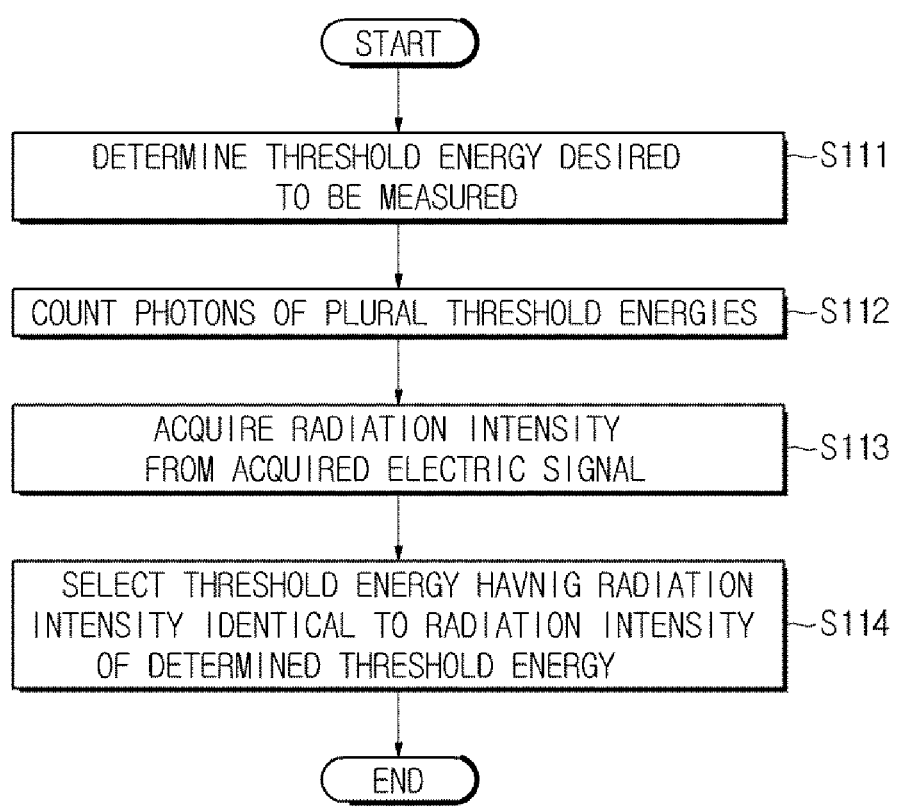
FIG. 8 is a flowchart showing a correction threshold energy acquisition operation in accordance with an exemplary embodiment.

Hereinafter, a process of acquiring the correction threshold energy $E_c$ at the threshold energy processor 50 in accordance with an exemplary embodiment will be described with reference to FIGS. 7 and 8. FIG. 8 is a flowchart showing an operation of acquiring a correction threshold energy $E_c$ in accordance with an exemplary embodiment.

A method of acquiring the correction threshold energy $E_c$ in accordance with an exemplary embodiment is as follows. First, a predetermined threshold energy $E_o$ that is to be used by the comparator p142 is determined by user selection or an additional setting (S111). The intensity of radiation or the normalized intensity of radiation at the predetermined threshold energy $E_o$ is calculated through a theoretical method or a simulation model (see FIG. 7 ①).

Radiation is emitted to the sample ob1 in a state that the predetermined threshold energy $E_o$ is determined. At least one threshold energy is converted to a threshold voltage V by use of the above described keV-mV relation, and the photons are counted using the converted threshold voltage V to output a counting result with respect to the at least one threshold energy (S 112). The at least one threshold energy may be identical to or different from the predetermined threshold energy $E_o$.

By using the counting result with respect to the at least one threshold energy output from the photon counter p143, at least one radiation intensity I with respect to the radiation passing through a predetermined object, that is, the sample ob1 is measured (S113). In accordance with an exemplary embodiment, a normalized intensity of radiation is measured using the radiation intensity I and an emitted radiation intensity $I_o$.

The threshold energy processor 50 compares the at least one measured radiation intensity I with the radiation intensity at the predetermined threshold energy $E_o$ or compares the normalized radiation intensity for the at least one measured radiation intensity with the normalized radiation intensity of the predetermined threshold energy $E_o$, thereby checking the coincidence as a result of comparison (see FIG. 7 ②).

Thereafter, the threshold energy processor 50 selects a threshold energy, at which a radiation intensity identical to the radiation intensity of the predetermined threshold energy $E_o$ or the normalized radiation intensity of the predetermined threshold energy $E_o$ is measured, among the at last one threshold energy obtained in operation S 112, thereby determining the selected threshold energy as the correction threshold energy $E_c$ (see FIG. 7③ and operation S114).

Accordingly, the correction threshold energy $E_c$ for the predetermined threshold energy $E_o$ is acquired.

As the correction threshold energy $E_c$ is acquired, the threshold energy processor 50 stores the acquired correction threshold energy $E_c$ in the database 30 as shown in FIGS. 1 and 5.

The database 30 may store information about the predetermined threshold energy $E_o$, for which the correction threshold energy $E_c$ is used, together with the correction threshold energy $E_c$. The correction threshold energy $E_c$ stored in the database 30 may be used when the subject ob2, for example, a human body is photographed, that is, used in operation S200 of capturing a radiation image as shown in FIGS. 1 and 2.

The threshold energy processor 50 may acquire the correction threshold energy $E_c$ for the predetermined threshold energy $E_o$, according to a material composition of the photographed object.

In a case that the correction threshold energy $E_c$ for the predetermined threshold energy $E_o$ is acquired according to the material composition of the photographed object, the database 30 may store information about the material composition of the photographed object together with the correction threshold energy $E_c$ for the predetermined threshold energy $E_o$.

In addition, the threshold energy processor 50 in accordance with an exemplary embodiment may acquire at least one correction threshold energy $E_c$ for at least one threshold energy $E_0$ each of the pixels p1 to p4 of the radiation detecting panel p. In this case, the database 30 may store the correction threshold energy $E_c$ and information about a corresponding one of the pixels p1 to p4, for which the correction threshold energy $E_c$ is used.

In addition, the threshold energy processor 50, in a case that a plurality of correction threshold energies $E_c$ are acquired with respect to a plurality of pixels p1 to p4, may generate a threshold energy map based on the plurality of threshold energies $E_c$ for the plurality of pixels p1 to p4, and store the generated threshold energy map in the database 30 so as to be used in operation S200 of capturing the radiation image.

Referring again to FIG. 3, operation S100 of acquiring prior information may further include acquiring radiation intensities of a plurality of threshold energies (S 120).

Even if the predetermined correction threshold energy $E_c$ is acquired for the predetermined threshold energy $E_o$ as the above, information about the material composition of an object to be photographed may be acquired depending on situations. For example, the graph between the photon energy and the radiation intensity as shown in FIGS. 6 and 7 may be different with the material composition of an object.

Figure 9:
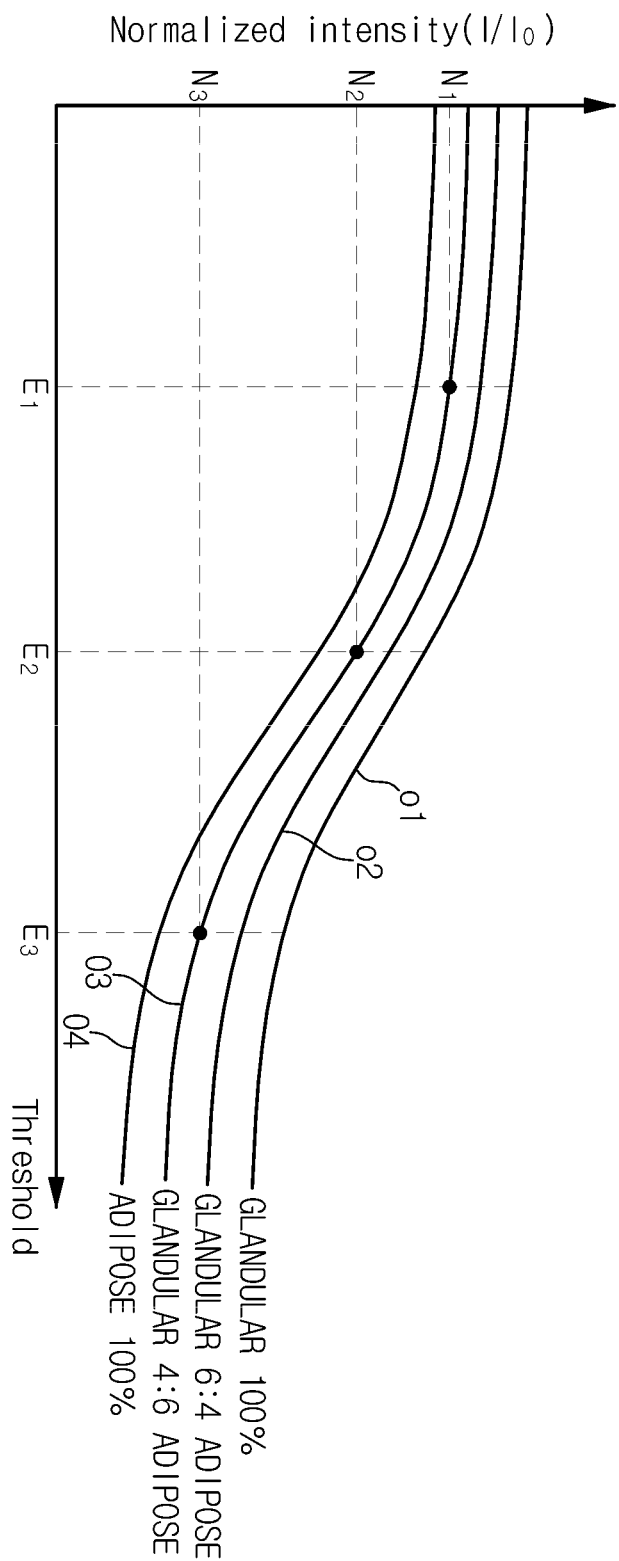
FIG. 9 is a graph showing a relationship between the threshold energy and the radiation intensity according to different material compositions.

FIG. 9 is a graph showing a relationship between the threshold energy and the normalized radiation intensity according to different material compositions.

Referring to FIG. 9, the curve of the threshold energy and the normalized radiation intensity may be different according to the material composition of an object to be photographed. For example, when an object that is entirely composed of glandular is photographed, a curve o1 between the threshold energy and the normalized radiation intensity is located above curves o2 to o4 each representing the relationship of the threshold energy and the normalized radiation intensity for an object including adipose tissue.

That is, for the same threshold energy $E_1$ to $E_3$, the more glands that are included in the object, the higher the normalized radiation intensity.

Figure 10:
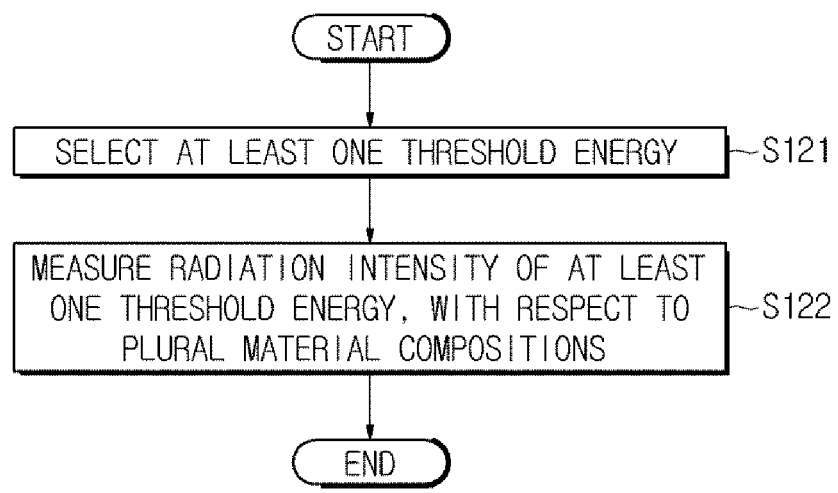
FIG. 10 is a flowchart showing a method of acquiring prior information in order to determine a material composition of an object in accordance with an exemplary embodiment.

FIG. 10 is a flowchart showing a method of acquiring prior information in order to determine a material composition of an object in accordance with an exemplary embodiment.

Referring to FIG. 10, in order to determine the material composition, at least one threshold energy $E_1$ to $E_3$ is selected to determine the material composition (S121). In this case, the at least one threshold energy may include the predetermined threshold energy $E_0$ described above.

Thereafter, a radiation intensity at the selected at least one threshold energy $E_1$ to $E_3$ is acquired with respect to a plurality of various material compositions (S122). For example, a radiation intensity of the at least one threshold energy $E_1$ to $E_3$ is measured with respect to various types of objects, various thicknesses of objects or various ratios of material compositions, thereby acquiring a plurality of radiation intensities.

The radiation intensity of at least one threshold energy $E_1$ to $E_3$ acquired according to the plurality of various material compositions may be stored in the database 30. In this case, information about a material composition corresponding to the radiation intensity of at least one threshold energy $E_1$ to $E_3$ may be stored in the database 30 together with the radiation intensity. If necessary, the radiation intensity of at least one threshold energy $E_1$ to $E_3$ may be stored in the form of a function or a graph representing the relationship between the threshold energy $E_1$ to $E_3$ and the radiation intensity.

In a case that the information about the material composition is acquired, information about the relationship between the acquired threshold energy $E_0$ and the correction threshold energy $E_c$ according to each material composition may be stored in the database 30.

The information acquired as the above is used to identify the material composition of the inside of an object to be photographed in operation S200. In accordance with another exemplary embodiment, the correction threshold energy $E_c$ may be acquired after the material composition is acquired.

Referring again to FIGS. 1 and 2, the control method of the radiation imaging apparatus may further include capturing a radiation image (see FIG. 1(b) and operation S200 in FIG. 2).

In operation S200 of capturing a radiation image, when a radiation image is generated through the radiography or a generated radiation image is calibrated, the prior information acquired as the above, for example, the correction threshold energy $E_c$ and the plurality of threshold energies $E_1$ to $E_3$ are used to generate a radiation image or to calibrate a generated radiation image.

Figure 11:
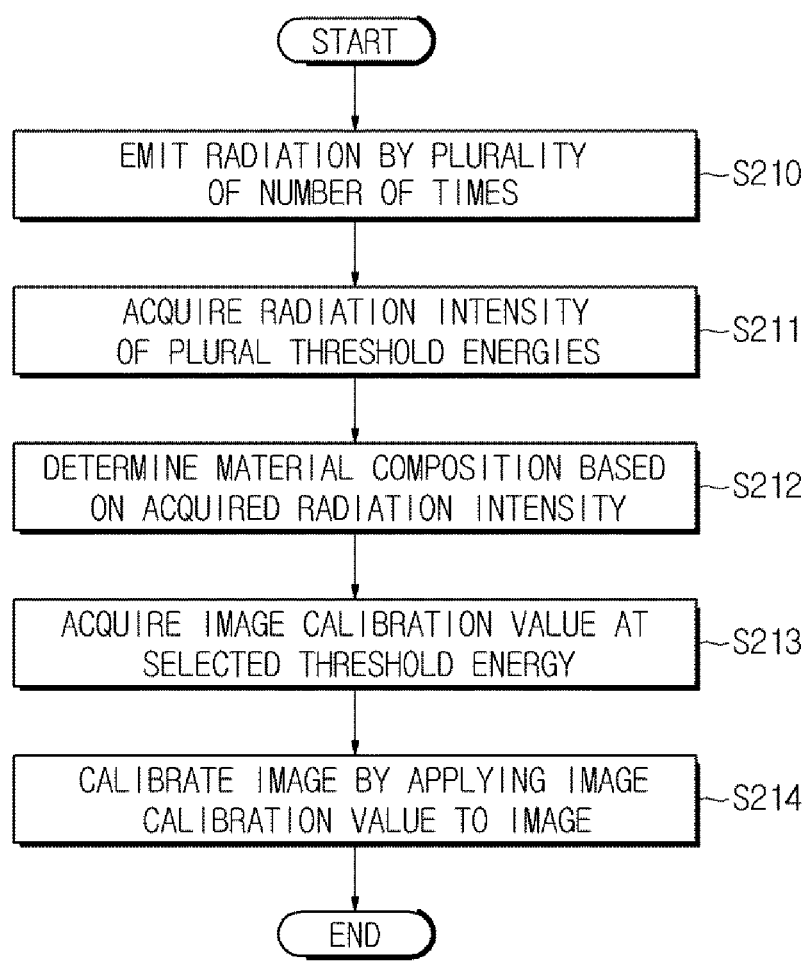
FIG. 11 is a flowchart showing a radiation image capturing operation in accordance with an exemplary embodiment.

FIG. 11 is a flowchart showing a radiation image capturing operation in accordance with an exemplary embodiment.

Referring to FIG. 11, in operation S200 (FIG. 2) of capturing a radiation image in accordance with an exemplary embodiment, radiation is emitted on an object, for example, the subject ob2, multiple times (S210). In the case that the radiation is emitted multiple times, the threshold energies $E_1$ to $E_3$ used by the photon counter p14 may be set to be different at each emission. Meanwhile, the subject ob2, which is subject to the emission, is an object for which a radiation image needs to be generated, for example, a human body. The subject ob2 may be different from or identical to the above described sample ob1.

If the radiation is emitted, the radiation is entirely or partially absorbed inside of the subject ob2, and the remaining radiation after being absorbed reaches the radiation detector 20. If the subject ob2 does not exist on the path of the radiation, all or most of the radiation may directly reach the radiation detector 20.

If the radiation reaches the radiation detector 20, the radiation detecting panel p of the radiation detector 20 receives the radiation. Referring to FIG. 5, the scintillator p11 of the radiation detecting panel p outputs a visible ray photon corresponding to the received radiation, and the photo conductor p13 having received the output visible ray photon outputs an electric signal corresponding to the output visible ray photon. In this case, the electric signal which is output may be different from the ideal electric signal due to the hardware characteristics as described above. In other words, the keV-mV relation may be different at each pixel p1 to p4.

The photon counter p14 receives the electric signal, and amplifies the received electric signal through the amplifier p141 and transmits the amplified signal to the comparator p142.

The comparator p142 compares the electric signal with the threshold energy $E_0$ that is set in operation S210, and may output a signal having a value of 1 or a signal having a value of 0 according to the result of comparison. As described above, in order to compare the predetermined threshold energy $E_0$ with the electric signal, the comparator p142 may convert the predetermined threshold energy $E_0$, the threshold voltage V through the keV-mV relation, and compare the converted threshold voltage with the received electric signal so that a signal of 1 or 0 is output.

The counter p143 counts the number of photons using the signal of 1 or 0 which is output, and outputs information about the counting result, that is, the radiation intensity. Accordingly, the radiation intensity for the radiation is measured. Since the radiation is emitted to the object multiple times as described in operation S210, and the threshold energies $E_1$ to $E_3$ are set to be different at each emission of radiation, and thus a plurality of radiation intensities are measured at different threshold energies $E_1$ to $E_3$ (S211).

The radiation intensity output from the photon counter p14 of the radiation detector 20 is transmitted to the image processor 40.

In the radiation image capturing operation in accordance with an exemplary embodiment, the material composition of the subject ob2 may be determined based on a plurality of radiation intensities before the image calibration value is obtained (S212).

Figure 12:
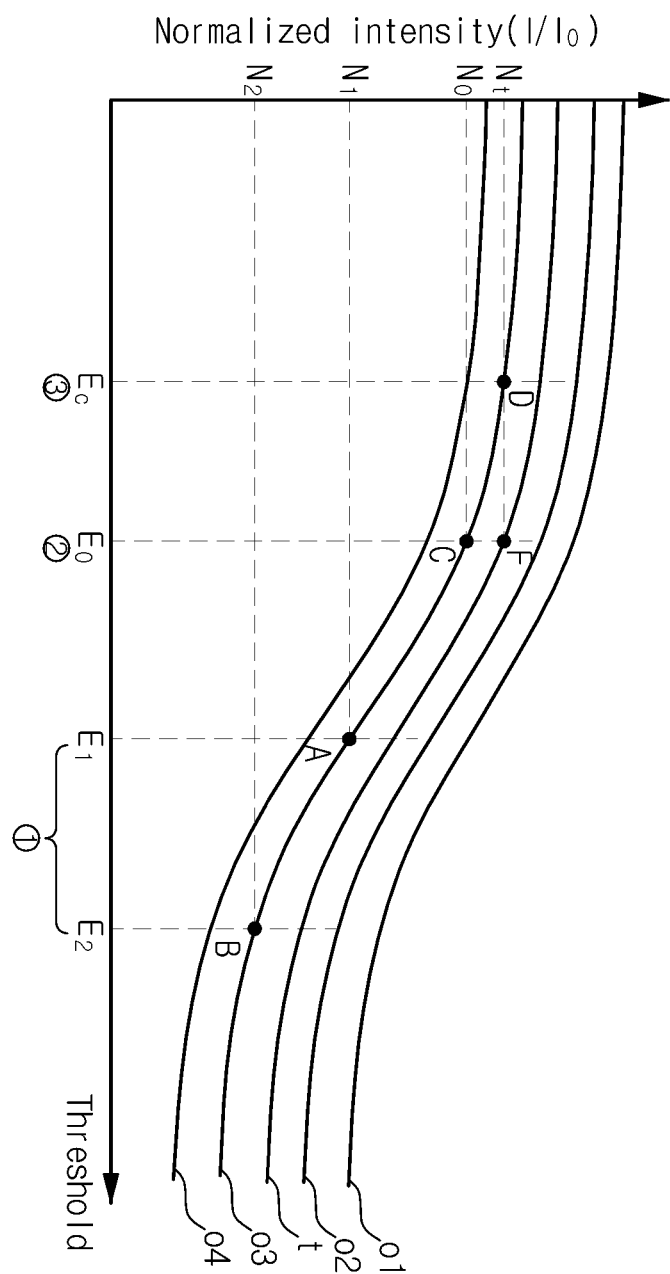
FIG. 12 is a graph used to explain a radiation image calibration.

FIG. 12 is a graph used to explain radiation image calibration.

Referring to FIG. 12, if radiation intensities $N_1$ and $N_2$ are measured at a plurality of threshold energies $E_1$ to $E_2$, respectively, the material composition is determined by use of the relationship between the plurality of threshold energies $E_1$ to $E_2$ and the measured radiation intensities (①).

For one example, the material composition of the subject ob2 may be determined by detecting the information about the material composition corresponding to the radiation intensities $N_1$ and $N_2$ measured for the threshold energies $E_1$ to $E_2$ by referring to the above described database 30. For another example, as shown in FIG. 12, the material composition of the subject ob2 may be determined by detecting a function or a graph, to which the radiation intensities $N_1$ and $N_2$ for the plurality of threshold energies $E_1$ to $E_2$ are substituted, among the functions and graphs with respect to the threshold energy and the radiation intensity acquired in operation S120 of acquiring the radiation intensities for a plurality of threshold energies. As shown in FIG. 12, a third graph o3 is determined as a graph corresponding to the radiation intensities $N_1$ and $N_2$ measured at the selected threshold energies $E_1$ to $E_2$.

If the material composition is determined and the relationship between the threshold energy and the radiation intensity, for example, the graph o3 shown in FIG. 12 is determined, an image calibration value at the selected threshold energy $E_0$ is determined based on the determined relationship between the threshold energy and the radiation intensity (S213 of FIG. 11).

For example, as shown in FIG. 12, if the relationship between the threshold energy and the radiation intensity measured in practice according to the material composition is determined as the third graph o3, the predetermined threshold energy $E_0$, which has been used by the comparator p142, and the third graph o3 are used (②) in determining the correction threshold energy $E_c$ (③). In this case, the correction threshold energy $E_c$ may be determined by referring to the information stored in the above described database 30.

In detail, as shown in FIG. 12, if the predetermined threshold energy $E_o$ and the third graph o3 are determined, the correction threshold energy $E_c$, at which a radiation intensity identical to the radiation intensity $N_t$ (see point C) of the predetermined threshold energy $E_0$ is measured, is determined by use of a relationship between a predetermined threshold energy $E_0$ and a correction threshold energy $E_c$, the relationship stored in the database 30 (see point D).

By use of the predetermined threshold energy $E_0$ and the correction threshold energy $E_c$, the image calibration value is acquired. For example, the image calibration value may be determined as a ratio of the predetermined threshold energy $E_0$ to the correction threshold energy $E_c$. The image calibration value may be determined as equation 3 below.

$$\rho = \frac{E_c}{E_0} \qquad \text{[Equation 3]}$$

P represents an image calibration value, and $E_0$ represents a predetermined threshold energy and Ec represents a correction threshold energy for the predetermined threshold energy.

If the image calibration value is determined as the above, the image processor 40 reflects the image calibration value on a radiation image which is generated or on a radiation which is to be generated, so that a radiation image is calibrated or a calibrated radiation image is generated (S214 of FIG. 11). For example, the image processor 40 generates a radiation image based on the radiation intensity and then performs calibration on the generated image by reflecting the image calibration value on the generated image, thereby generating a calibrated image. Alternatively, image calibration is reflected on a radiation intensity prior to generation of a radiation image and a calibrated image having the image calibration value reflected thereon is generated.

As a result, the radiation imaging apparatus may acquire an ideal condition radiation image, from which an error due to hardware defects of the radiation imaging apparatus is calibrated.

The acquired radiation image may be stored in a storage 60 configured to store images as shown in FIG. 1, for example, an internal memory device and an external memory device, such as memories, or according to a setting made by a user or a predetermined setting. The acquired radiation image may be displayed on a display d that is provided on the radiation imaging apparatus or connected to the radiation imaging apparatus through a wired/wireless communication network.

Hereinafter, a digital radiography apparatus in accordance with an exemplary embodiment will be described with reference to FIGS. 13 to 17.

Figure 13:
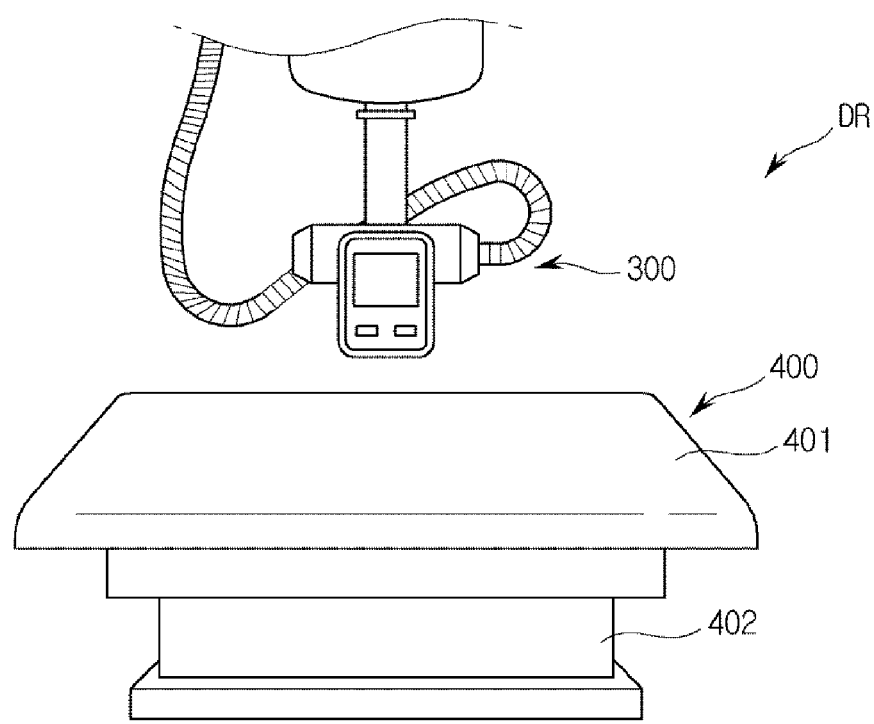
FIG. 13 is a front view of a digital radiography apparatus in accordance with an exemplary embodiment.
Figure 14:
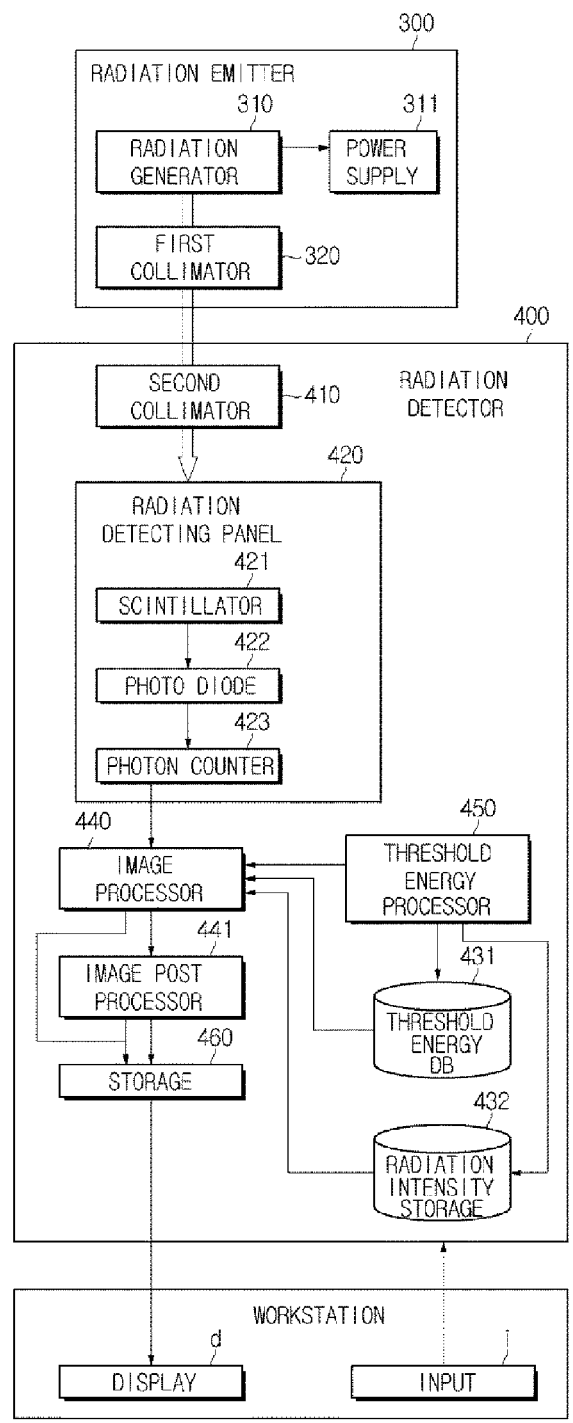
FIG. 14 is a block diagram of a digital radiography apparatus in accordance with an exemplary embodiment.

FIG. 13 is a front view of a digital radiography apparatus in accordance with an exemplary embodiment. FIG. 14 is a block diagram of a digital radiography apparatus in accordance with an exemplary embodiment.

The radiation imaging apparatus in accordance with an exemplary embodiment described in FIG. 13 will be referred to as a digital radiography (DR) apparatus. Hereinafter, the following description will be made in relation to a digital radiography apparatus DR with reference to FIGS. 13 to 17 as an example of the radiation imaging apparatus. However, the radiation imaging apparatus in accordance with an exemplary embodiment is not limited thereto, and may be applied to a mammography apparatus or a computed tomography (CT) apparatus.

Referring to FIGS. 13 and 14, the digital radiography apparatus includes a radiation emitter 300 to emit radiation, and a radiation detector 400 on which a sample ob1 or a subject ob2, such as a human body, is placed and which is configured to receive a radiation passing through the sample ob1 or the subject ob2 or to directly receive radiation from the radiation emitter 300.

The radiation emitter 300 includes a radiation generator 310, a power supply 311 and a first collimator 320.

Figure 15:
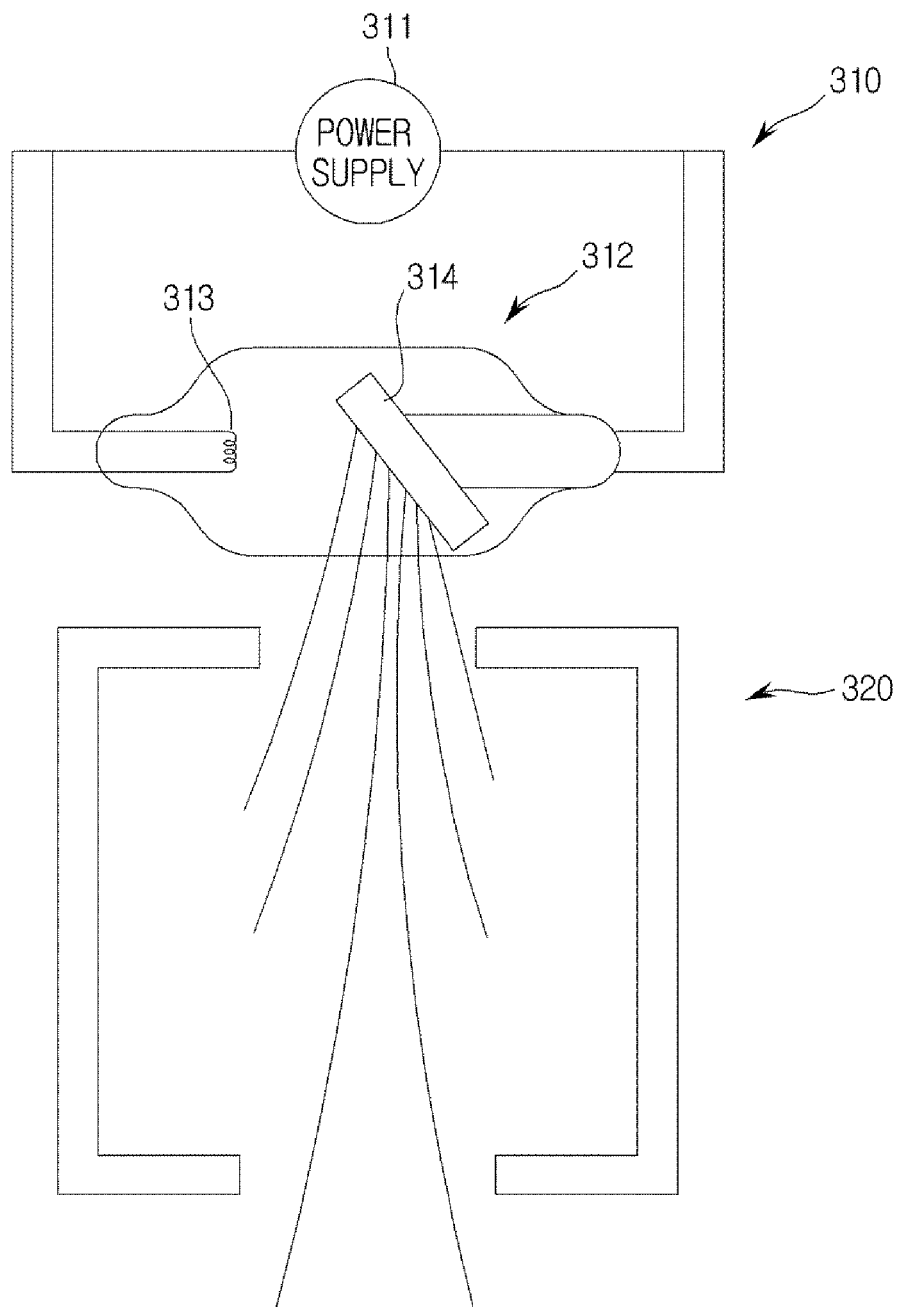
FIG. 15 is a diagram illustrating the configuration of a radiation emitter in accordance with an exemplary embodiment.

FIG. 15 is a structural view of a radiation emitter in accordance with an exemplary embodiment. Referring to FIG. 15, the radiation generator 310 of the radiation emitter 300 includes a radiation tube 312 (cathode ray tube) to generate radiation having an energy level corresponding to a voltage applied from the power supply 311.

The cathode tube 312 includes an anode 314 and a cathode filament 313. If a predetermined voltage is applied from the power supply 311 to the radiation tube 312, an electron of the cathode filament 313 of the radiation tube 312 is moved while being accelerated toward the anode 314. When the accelerated electron is rapidly decelerated due to the coulomb force at an area adjacent to the anode 314, a predetermined radiation, for example, an X-ray, is generated from the anode 314 according to the principle of the conservation of energy.

In this case, the amount of energy from radiation generated from the radiation tube 312, that is, the energy level, is determined by a voltage applied from the power supply 311. In detail, if a low voltage is applied to two opposite ends of the radiation tube 312, the electron inside of the radiation tube 312 is slowly accelerated, and thus radiation having low energy is generated from the anode 314. On the other hand, if a high voltage is applied to the radiation tube 312, the electron is rapidly accelerated, and thus radiation having high energy is generated from the anode 314. The radiation generated from the anode 314 of the radiation tub 312 is emitted toward the radiation detector 400 on which the sample ob1 or the subject ob2 is placed.

The power supply 311 is electrically connected to the radiation tube 312, and applies a predetermined voltage to the radiation tube 312 according to an external control command.

The radiation generated from the radiation generator 310 may pass through the first collimator 320 before being emitted to the sample ob1 or the subject ob2. The first collimator 320 is an apparatus configured to guide a direction or a range of radiation emission. The first collimator 320 may determine the direction or range of radiation emission by blocking the radiation in a manner to absorb the radiation emitted other than in an unintended direction. To this end, the first collimator 320 may include a collimator filter or a collimator blade formed of metal capable of absorbing radiation, for example, plumbum (Pb) or lead.

The radiation detector 400, as shown in FIG. 13, may include a stand 401 on which the sample ob1 or the subject ob2, such as a human body, is placed, and a support 402 to support the stand 401. A radiation detecting panel 420 may be disposed at a lower end of the stand 401 of the radiation detector 400 to detect the radiation. In accordance with another exemplary embodiment, the radiation detecting panel 420 may be designed so as to enable movement to properly receive the emitted radiation.

A second collimator 410 may be installed at the radiation detecting panel 420. The radiation may be scattered according to the characteristics of the inside of the sample ob1 or the subject ob2 while passing through the sample ob1 or the subject ob2. The second collimator 410 removes the radiation that is scattered while passing through the subject ob2, thereby enabling a proper amount of radiation to reach the radiation detecting panel 420. The second collimator 410 may include a plurality of partition walls formed of metal, capable of absorbing the radiation, for example, plumbum (Pb).

The radiation detecting panel 420 may include a plurality of pixels p, and each pixel p may respectively include a scintillator 421, a photo diode 422 and a photon counter 423.

The scintillator 421 outputs a visible ray photon corresponding to the incident radiation, and transmits the visible ray photon to the photo diode 422.

The photo diode 422 receives the visible ray photon, and outputs an electric signal corresponding to the received visible ray photon.

The photon counter 423 compares the electric signal output from the photo diode 422 with a predetermined threshold energy $E_0$ to count electric signals, wherein each having an energy exceeding the threshold energy, thereby measuring a radiation intensity I.

Meanwhile, the radiation detector 400 may further include an image processor 440, an image post processor 441, a threshold energy processor 450 and a storage 460. In accordance with an exemplary embodiment, the image processor 440, the image post processor 441, the threshold energy processor 450 and the storage 460 may be provided at the radiation detector 400. In accordance with another exemplary embodiment, the image processor 440, the image post processor 441, the threshold energy processor 450 and the storage 460 may be provided at an information processing device, such as a workstation or a server device connected to the radiation detector 400 through a wired/wireless scheme.

The threshold energy processor 450 in accordance with an exemplary embodiment acquires a correction threshold energy $E_c$ corresponding to a threshold energy $E_0$, which is to be used at the photon counter 423, and stores the acquired correction threshold energy $E_c$ in a threshold energy database 431. The correction threshold energy $E_c$ represents a threshold energy having a measured radiation intensity identical to an ideal radiation intensity, which is measured at a predetermined threshold energy $E_0$.

The threshold energy processor 450 in accordance with an exemplary embodiment receives data about a radiation intensity I or a normalized radiation intensity $I_{normal}$ from the photon counter 423. If necessary, the threshold energy processor 450 may calculate a normalized radiation intensity $I_{normal}$ by using a received radiation intensity I and a radiation intensity $I_0$, which is obtained before passing through the sample ob1 or the subject ob2.

Meanwhile, the threshold energy processor 450 in accordance with an exemplary embodiment may receive a theoretical radiation intensity $I_{theoretical}$ at a predetermine threshold energy $E_0$, which has been used at the photon counter 423. In this case, the theoretical intensity $I_{theoretical}$ at the predetermine threshold energy $E_0$ may be delivered from a controller or a storage external to the radiation detector 400. In accordance with another embodiment, the threshold energy processor 450 may calculate the theoretical radiation intensity $I_{theoretical}$ based on the predetermined threshold energy $E_0$.

In addition, the threshold energy processor 450 may receive data about the predetermined threshold energy $E_0$ from an additional controller, an additional storage or the photon counter 423.

The threshold energy processor 450 may compare the radiation intensity I transmitted from the photon counter 423 with the theoretical radiation intensity $I_{theoretical}$, or may compare the normalized radiation intensity $I_{normal}$ transmitted from the photon counter 423 with the theoretical normalized radiation intensity $I_{NT}$, thereby measuring the correction threshold energy $E_c$. In this case, the curves of the threshold energy and the normalized radiation intensity shown in FIGS. 6 and 7 may be used.

If the photon counter 423 outputs a fourth threshold intensity $I_4$ to a sixth threshold intensity $I_6$ by comparing a fourth threshold energy $E_4$ to a sixth threshold energy $E_6$ with an electric signal, the threshold energy processor 450 in accordance with an exemplary embodiment compares the output fourth radiation intensity $I_4$ to the sixth radiation intensity $I_6$ with the theoretical radiation intensity $I_{theoretical}$ at the predetermined threshold energy (C) so as to detect a threshold energy having a radiation intensity identical to the theoretical radiation intensity $I_{theoretical}$. For example, the threshold energy processor 450 detects the fourth threshold energy (C) and determine the detected fourth threshold energy $E_4$ as the correction threshold energy $E_c$, thereby measuring the correction threshold energy $E_c$ corresponding to the predetermined threshold energy $E_0$.

The measured correction threshold energy $E_c$ may be stored in the threshold energy database 431.

In addition, with respect to at least one threshold energy for a plurality of various material compositions, for example, with respect to a first energy to a third energy $E_1$ to $E_3$, the threshold energy processor 450 further acquires a first radiation intensity $I_1$ to a third radiation intensity $I_3$, and stores the acquired first radiation intensity $I_1$ to the third radiation intensity $I_3$ with respect to the first to third energies $E_1$ to $E_3$ in a radiation intensity storage 432. In accordance with an exemplary embodiment, the at least one threshold energy may include the predetermined threshold energy $E_0$, for which a radiation intensity identical to a radiation intensity of the correction threshold energy (C) is theoretically calculated.

When a subject ob2 is photographed, the stored first to third radiation intensities $I_1$ to $I_3$ with respect to the first to third energies $E_1$ to $E_3$ are used to select an appropriate threshold energy-to normalized radiation intensity curve, according to the material composition of the subject ob2. That is, the stored first to third radiation intensities $I_1$ to $I_3$ are used to determine the material composition of the subject ob2.

The measuring and storing of the correction threshold energy $E_c$ by the threshold energy processor 450, and the acquiring of the threshold energies $E_1$ to $E_3$ for a plurality of material compositions are performed during a calibration process of the radiation imaging apparatus.

The image processor 440 generates a radiation image according to the radiation intensity measured by the photon counter 423.

As the correction threshold energy $E_c$ and the threshold energies $E_1$ to $E_3$ for a plurality of various material compositions are acquired by the threshold energy processor 450, the image processor 440 generates a radiation image or calibrates a generated radiation image based on the correction threshold energy $E_c$ and the threshold energies $E_1$ to $E_3$ for the plurality of various material compositions.

In accordance with an exemplary embodiment, the image processor 440 generates a radiation image based on a radiation intensity that is measured according to a predetermined threshold energy $E_0$ received from the photon counter 423, and calibrates the generated radiation image based on the correction threshold energy $E_c$ or based on the correction threshold energy $E_c$ and the threshold energies $E_1$ to $E_3$ for the plurality of various material compositions.

The image processor 400 in accordance with an exemplary embodiment receives a radiation intensity for a predetermined subject ob1 that is acquired according to a predetermined threshold energy $E_0$, and generates a radiation image according to the received radiation intensity. In this case, the image processor 400 generates a radiation image in a manner to display a pixel of an image, which corresponds to a pixel having a stronger radiation intensity, to be darker.

Meanwhile, the image processor 440 in accordance with an exemplary embodiment may further receive radiation intensities at a plurality of threshold energies $E_1$ to $E_3$ in addition to the radiation intensity at the predetermined threshold energy $E_0$ used for the image generation.

The image processor 440 receives radiation intensities $I_1$ to $I_3$ measured at the at least one threshold energy $E_1$ to $E_3$ with respect to a plurality of various material compositions from the threshold energy processor 450 or the radiation intensity storage 432, and compares the received radiation intensities $I_1$ to $I_3$ with a radiation intensity acquired according to a plurality of threshold energies $E_1$ to $E_3$, thereby determining the material composition of the subject ob2. The predetermined threshold energy $E_0$ for generating an image according to a user's selection or a predetermined setting also may be used to determine the material composition of the subject ob2. In this case, the image processor 440 may receive a radiation intensity of a predetermined threshold energy $E_0$ with respect to a plurality of various materials from the threshold energy processor 450 or the radiation intensity storage 432.

As described in FIG. 9, the curve between the threshold energy and the normalized radiation intensity may be different based on the material composition of the object to be photographed. In this case, the image processor 440 determines the material composition by detecting an appropriate curve between a threshold energy and a normalized radiation intensity based on the radiation intensities $I_1$ to $I_3$ for at least one threshold energy $E_1$ to $E_3$ measured with respect to a plurality of material compositions.

The determining of the material composition in accordance with an exemplary embodiment may be performed by the image processor 440, or may be performed by the threshold energy processor 450.

The image processor 440 receives the correction threshold energy $E_c$ corresponding to the predetermined threshold energy $E_0$ from the threshold energy processor 450 or the threshold energy database 431. In this case, the correction threshold energy $E_c$ corresponding to the predetermined threshold energy $E_0$ is determined by the photo energy-to-normalized radiation intensity curve corresponding to the determined material composition.

The image processor 400 generates an image calibration value by use of the predetermined threshold energy $E_0$ and the correction threshold energy $E_c$. For example, the image calibration value is determined by a ratio between the predetermined threshold energy $E_0$ and the correction threshold energy $E_c$ described above through equation 3.

As described above, even if the radiation intensity is measured by comparing the predetermined threshold energy $E_0$ with the electric signal, the acquired radiation intensity may be different from the radiation intensity in an ideal condition due to the hardware characteristics of the radiation detecting panel or various circuits. For example, the keV-mV relation for each pixel is determined differently between pixels, so the keV-mV may be different from a keV-mV used at the photon counter 423. Accordingly, by calibrating a radiation image, which is generated in a state that the predetermined threshold energy $E_0$ is set, by use of the relationship between the predetermined threshold energy $E_0$ and the correction threshold energy $E_c$, a radiation image in an ideal condition is acquired.

The image process 400 generates an image correction value, but in accordance with another exemplary embodiment, the threshold energy processor 450 may generate an image calibration value, and transmit the generated image calibration value to the image processor 400.

Although the above description has been made in relation to the image processor 400 generating a radiation image from an input radiation intensity and applying an image calibration value to the generated radiation image, the exemplary embodiment is not limited thereto. For example, the image processor 400 acquires an image calibration value before generating a radiation image, applies the image calibration value to an input radiation intensity, and generates a radiation image from the radiation intensity having the image calibration value applied thereto.

The radiation image generated or calibrated by the image processor 440 is transmitted to the image post processor 441, the storage 460 or the display d.

The image post processor 441 may further calibrate the calibrated radiation image by modifying the brightness, contrast and sharpness of the radiation image output after being calibrated from the image post processor 441. In addition, the image post processor 441 may perform post processing on a radiation image by applying other various types of image post-processing operations on the calibrated radiation image. In addition, the image post processor 441 may generate a three-dimensional radiation image by use of a calibrated radiation image. The radiation image having been subject to the post-processing is transmitted to the storage 460 or the display d provided on the workstation.

The storage 460 stores the calibrated radiation image output from the image processor 440 or the post-processed radiation image output from the image post processor 441.

An input i receives commands for radiography or various instruction or commands for image processing, or various information such as the number of occurrences of radiation emission, and transmits the commands, instruction and information to the radiation emitter 300 or the radiation detector 400. In addition, the input i may receive information about the predetermined threshold energy $E_0$. The input i may be installed at an additional workstation as shown in FIG. 14, or may be directly provided on the radiation detector 400.

The display d displays the calibrated radiation image or the post-processed radiation image. The display d may receive a radiation image directly from the image processor 440 or the image post processor 441 and display the received radiation image, or may display a radiation image stored in the storage 460.

Figure 16:
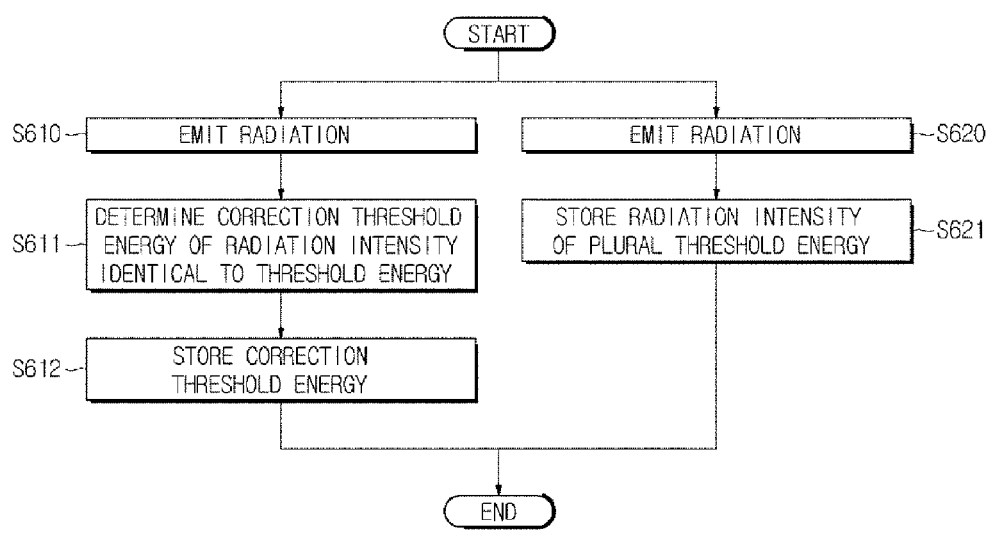
FIG. 16 is a flowchart showing a prior information acquisition operation of at a digital radiography apparatus in accordance with an exemplary embodiment.

Hereinafter, an operation of acquiring prior information at the digital radiography apparatus will be described. FIG. 16 is a flowchart showing a prior information acquisition operation at a digital radiography apparatus in accordance with an exemplary embodiment.

First, radiation is emitted to the sample ob1 which is used to acquire the prior radiation information. The radiation detecting panel 420 of the radiation detector 400 receives the incident radiation and converts the received radiation into an electric signal. The converted electric signal is compared with a threshold energy, thereby outputting a radiation intensity (S610).

A predetermined threshold energy $E_0$, for which a radiation intensity identical to the output radiation intensity is theoretically calculated, is determined. In this case, the threshold energy used in operation S610 is determined as a correction threshold energy $E_c$ for the determined predetermined threshold energy. Accordingly, the correction threshold energy $E_c$ having the identical radiation intensity to that of the predetermined threshold energy $E_0$ is determined (S611).

The predetermined threshold energy $E_0$ and the determined correction threshold energy $E_c$ are then stored (S612).

Radiation intensities at various material compositions are acquired in a manner to replace the above sample ob1 with another sample ob1 composed of a different material from that of the above sample ob1, and then emit radiation to the replaced sample ob1 (S620). In this case, the radiation intensity may be acquired by comparing a plurality of various threshold energies with the electric energy output from the radiation detector 400.

The radiation intensities at the plurality of threshold energies with respect to various material compositions are stored (S621).

Accordingly, the prior information for calibration at the radiation imaging apparatus is acquired.

Figure 17:
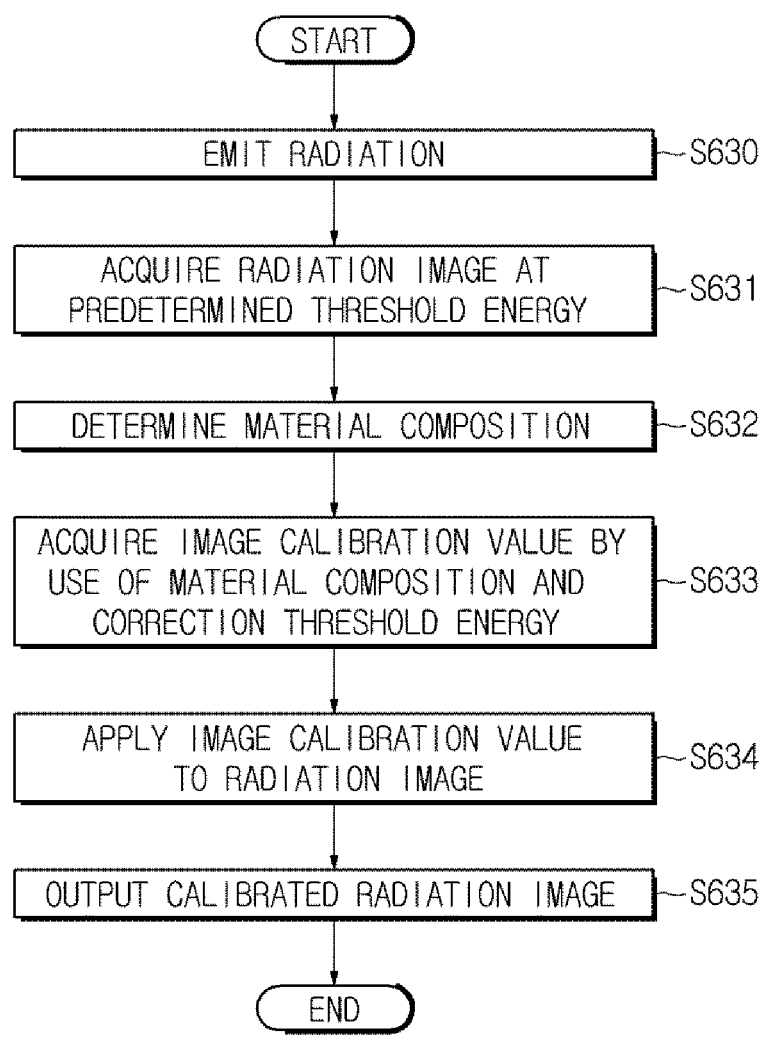
FIG. 17 is a flowchart showing a calibration operation after an image capture at a digital radiography apparatus in accordance with an exemplary embodiment.

Hereinafter, a digital radiography operation will be described with reference to FIG. 17. FIG. 17 is a flowchart showing a digital radiography operation at a digital radiography apparatus in accordance with an exemplary embodiment.

After the acquisition of the prior information for the radiograph apparatus is completed, radiation is emitted to a subject ob2 to be examined (S630).

The radiation detector 400 receives the radiation passing through the subject ob2, and converts the received radiation into an electric signal. The converted electric signal is compared with a predetermined threshold energy $E_0$ that is used for radiation image generation. The number of cases in which the electric signal is greater than the predetermined threshold energy or a voltage of the predetermined threshold energy $E_0$ is counted as a result of comparison, so that the number of photons exceeding the threshold energy is counted, thereby obtaining the radiation intensity. By using the obtained radiation intensity, a radiation image at the predetermined threshold energy is acquired (S631).

A plurality of threshold energies $E_1$ to $E_3$ that is set in advance is compared with the converted electric signal to obtain a plurality of radiation intensities $I_1$ to $I_3$, and the material structure of the subject ob2 is determined by using the plurality of radiation intensities $I_1$ to $I_3$ (S632). In this case, the plurality of threshold energies may include the predetermined threshold energy $E_0$ that is used in practice to generate the radiation image.

The image calibration value is calculated by use of the photon energy-to-the normalized radiation intensity curve according to the determined material structure and the correction threshold energy $E_c$ acquired in operation S611, or by use of the photon energy-to-the normalized radiation intensity curve according to the determined material structure and the relationship between the predetermined threshold energy $E_0$ and the correction threshold energy $E_c$ (S633).

A calibrated radiation image is acquired by applying the calculated image calibration value to the acquired radiation image (S634).

The calibrated radiation image is then output through the display d (S635).

As a result, a radiation image, at which a radiation image artifact due to a hardware defect from the calibration of the digital radiography apparatus, is acquired. In addition, the threshold energy for acquiring the radiation intensity may be finely adjusted.

As apparent from the above description of the calibration method of the radiation detecting apparatus, the radiation imaging apparatus and the control method of the radiation imaging apparatus in accordance with an exemplary embodiment, more precise and desired images are obtained for inside of the object.

In addition, the threshold energy of the radiation detecting apparatus is finely adjusted, so that limitations on the precision of the threshold energy are overcome and also errors of the radiation threshold energy are minimized.

In addition, a control circuit of the radiation imaging apparatus or the radiation detecting apparatus is simplified, thereby ensuring convenience of design and reduction in the cost of the radiation imaging apparatus or the radiation detecting apparatus.

In addition, a superior quality of radiation image is obtained by use of the radiation imaging apparatus or the radiation detecting apparatus, as disclosed in the exemplary embodiments.

In addition, since the signal-to-noise ratio (SNR) of the radiation image is improved with only the same dose of radiation emission, the required dose does not need to be increased to obtain a high SNR. Accordingly, the exposure dose to an object, in particular, a human body, is reduced.

Although a few exemplary embodiments have been shown and described, it would be appreciated by those skilled in the art that changes may be made in these exemplary embodiments without departing from the principles and spirit of the disclosure, the scope of which is defined in the claims and their equivalents.

What is claimed is:

1. A method of controlling an x-ray radiation imaging apparatus, the method comprising:
performing prior information acquisition by obtaining at least one correction threshold energy, at which a theoretical x-ray radiation intensity of at least one predetermined threshold energy is measured, using a difference between an x-ray radiation intensity calculated in an ideal condition and an x-ray radiation intensity measured actually; and
performing x-ray radiation image acquisition using a photon counting x-ray radiation detector, by obtaining at least one x-ray radiation image using the at least one correction threshold energy,
wherein the at least one predetermined threshold energy and the at least one correction threshold energy indicate energies above which x-ray radiation is measured.

2. The method of claim 1, wherein in performing the prior information acquisition, an x-ray radiation intensity of the at least one correction threshold energy is obtained; and
in performing the x-ray radiation image acquisition, at least one x-ray radiation image at the at least one predetermined threshold energy is generated using the x-ray radiation intensity of the at least one correction threshold energy.

3. The method of claim 1, wherein in performing the prior information acquisition, x-ray radiation intensities of a plurality of threshold energies with respect to at least one material composition are obtained.

4. The method of claim 3, wherein the plurality of threshold energies comprises the at least one predetermined threshold energy.

5. The method of claim 3, wherein in performing the x-ray radiation image acquisition, a material composition of an object is determined using at least one of the plurality of threshold energies with the obtained x-ray radiation intensities.

6. The method of claim 5, wherein in performing the x-ray radiation image acquisition, at least one calibrated x-ray radiation image is generated at the at least one predetermined threshold energy using the determined material composition of the object and the at least one correction threshold energy.

7. The method of claim 1, wherein in performing the x-ray radiation image acquisition, an image calibration value is generated based on an x-ray radiation intensity of the at least one correction threshold energy, and at least one x-ray radiation image is generated at the at least one predetermined threshold energy using the image calibration value.

8. The method of claim 7, wherein in performing the x-ray radiation image acquisition, the image calibration value is generated based on a relationship between an x-ray radiation intensity of the correction threshold energy and an x-ray radiation intensity of the at least one predetermined threshold energy.

9. A method of controlling an x-ray radiation imaging apparatus, the method comprising:
performing radiography by emitting x-ray radiation onto an object, receiving, by a photon counting x-ray radiation detector, the x-ray radiation emitted onto the object and converting the received x-ray radiation into an electric signal; and
performing x-ray radiation image generation by generating at least one x-ray radiation image at an at least one predetermined threshold energy based on the electric signal, which is converted from the x-ray radiation, and the at least one predetermined threshold energy,
wherein at least one calibrated x-ray radiation image is generated using at least one correction threshold energy for the at least one predetermined threshold energy,
wherein the at least one correction threshold energy is obtained, using a difference between an x-ray radiation intensity calculated in an ideal condition and an x-ray radiation intensity measured actually, wherein the at least one correction threshold energy is a threshold energy at which a theoretical x-ray radiation intensity of the at least one predetermined threshold energy is measured, and wherein the at least one predetermined threshold energy and the at least one correction threshold energy indicate energies above which x-ray radiation is measured.

10. The method of claim 9, further comprising:
performing x-ray radiation intensity measurement by measuring an x-ray radiation intensity of the at least one predetermined threshold energy based on the electric signal converted from the x-ray radiation.

11. The method of claim 10, wherein in performing the x-ray radiation image generation, the at least one x-ray radiation image is calibrated using the x-ray radiation intensity of the at least one predetermined threshold energy and an x-ray radiation intensity of the at least one correction threshold energy for the at least one predetermined threshold energy.

12. The method of claim 9, further comprising:
performing an x-ray radiation intensity measurement by measuring x-ray radiation intensities of a plurality of threshold energies based on the electric signal converted from the x-ray radiation; and
performing a material composition determination by determining a material composition of the object using the measured x-ray radiation intensities of the plurality of threshold energies.

13. The method of claim 12, wherein in performing the x-ray radiation image generation, the x-ray radiation image of the at least one predetermined threshold energy is generated using an x-ray radiation intensity of the at least one correction threshold energy and the determined material composition of the object.

14. The method of claim 13, wherein in performing the x-ray radiation image generation, the x-ray radiation intensity of the at least one correction threshold energy is determined according to the x-ray radiation intensity of the at least one predetermined threshold energy and the determined material composition of the object, and the at least one x-ray radiation image is calibrated based on the determined x-ray radiation intensity of the at least one correction threshold energy.

15. A method of controlling a radiation imaging apparatus, the method comprising:
performing radiography by emitting radiation onto an object, receiving the radiation emitted onto the object and converting the received radiation into an electric signal;
performing radiation image generation by generating at least one radiation image at an at least one predetermined threshold energy based on the electric signal, which is converted from the radiation, and the at least one predetermined threshold energy,
wherein at least one calibrated radiation image is generated using at least one correction threshold energy for the at least one predetermined threshold energy,
wherein the at least one correction threshold energy is a threshold energy at which a theoretical radiation intensity of the at least one predetermined threshold energy is measured, and
wherein the at least one correction threshold energy is obtained using a difference between an x-ray radiation intensity calculated in an ideal condition and an x-ray radiation intensity measured actually;
performing a radiation intensity measurement by measuring radiation intensities of a plurality of threshold energies based on the electric signal converted from the radiation; and performing a material composition determination by determining a material composition of the object using the measured radiation intensities of the plurality of threshold energies,
wherein in performing the radiation image generation, the at least one radiation image of the at least one predetermined threshold energy is generated using a radiation intensity of the at least one correction threshold energy and the determined material composition of the object,
wherein in performing the radiation image generation, the radiation intensity of the at least one correction threshold energy is determined according to the radiation intensity of the at least one predetermined threshold energy and the determined material composition of the object, and the at least one radiation image is calibrated based on the determined radiation intensity of the at least one correction threshold energy, and
wherein in performing the radiation image generation, an image calibration value is generated based on the radiation intensity of the at least one predetermined threshold energy, the radiation intensity of the at least one correction threshold energy, and the determined material composition of the object, and the radiation image of the at least one predetermined threshold energy is calibrated using the generated image calibration value.

16. An x-ray radiation imaging apparatus comprising:
an x-ray radiation emitter configured to emit x-ray radiation onto an object;
a photon counting x-ray radiation detector configured to receive the x-ray radiation emitted from the x-ray radiation emitter and convert the received x-ray radiation into an electric signal according to at least one predetermined threshold energy; and
an image processor configured to generate an x-ray radiation image based on the electric signal, and calibrate the generated x-ray radiation image using at least one correction threshold energy for the at least one predetermined threshold energy,
wherein the at least one correction threshold energy is a threshold energy at which a theoretical x-ray radiation intensity of the at least one predetermined threshold energy is measured, and the at least one correction threshold energy is obtained using a difference between an x-ray radiation intensity calculated in an ideal condition and an x-ray radiation intensity measured actually, and
wherein the at least one predetermined threshold energy and the at least one correction threshold energy indicate energies above which the received x-ray radiation is converted.

17. The x-ray radiation imaging apparatus of claim 16, wherein the x-ray radiation emitter emits x-ray radiation onto the object a plurality of times, and determines a material composition of the object based on a plurality of threshold energies.

18. The x-ray radiation imaging apparatus of claim 17, wherein the image processor calibrates an x-ray radiation image at the at least one predetermined threshold energy using the determined material composition and the at least one correction threshold energy.

19. The x-ray radiation imaging apparatus of claim 17, wherein the image processor obtains the at least one correction threshold energy using the determined material composition of the object and the at least one predetermined threshold energy.

20. The x-ray radiation imaging apparatus of claim 17, wherein the image processor obtains an x-ray radiation intensity of the at least one correction threshold energy using the determined material composition of the object and an x-ray radiation intensity of the at least one predetermined threshold energy.

21. The x-ray radiation imaging apparatus of claim 16, wherein the image processor generates an image calibration value based on an x-ray radiation intensity of the at least one predetermined threshold energy and an x-ray radiation intensity of the at least one correction threshold energy, and calibrates the x-ray radiation image using the image calibration value.

* * * * *